(12) United States Patent
Wasylyk et al.

(10) Patent No.: US 7,537,887 B2
(45) Date of Patent: May 26, 2009

(54) NET, A TRANSCRIPTION FACTOR OF THE TCF FAMILY, AS REGULATOR OF ANGIOGENIC FACTOR EXPRESSION

(75) Inventors: Bohdan Wasylyk, Illkirch (FR); Marie-Christine Multon, Versailles (FR); Abdelkader Ayadi, Strasbourg (FR); Hong Zheng, Strasbourg (FR)

(73) Assignees: Aventis Pharma S.A., Paris (FR); Institut National de la Sante de la Recherche Medicale, Paris (FR)

(*) Notice: Subject to any disclaimer, the term of this patent is extended or adjusted under 35 U.S.C. 154(b) by 14 days.

(21) Appl. No.: 10/415,181

(22) PCT Filed: Oct. 23, 2001

(86) PCT No.: PCT/EP01/12987

§ 371 (c)(1),
(2), (4) Date: Oct. 3, 2003

(87) PCT Pub. No.: WO02/35235

PCT Pub. Date: May 2, 2002

(65) Prior Publication Data

US 2004/0053833 A1   Mar. 18, 2004

(30) Foreign Application Priority Data

Oct. 25, 2000   (EP)   ................... 00402968

(51) Int. Cl.
  *C12Q 1/00*   (2006.01)
  *C12Q 1/68*   (2006.01)
  *C12Q 1/02*   (2006.01)
  *C12Q 1/48*   (2006.01)
  *G01N 33/53*  (2006.01)

(52) U.S. Cl. .................. 435/6; 435/4; 435/29; 435/7.1; 435/15

(58) Field of Classification Search ........................ None
See application file for complete search history.

(56) References Cited

FOREIGN PATENT DOCUMENTS

WO   WO 99/67283   12/1999
WO   WO 00/02589   1/2000

OTHER PUBLICATIONS

Giovane et al. Net, a new ets transcription factor that is activated by Ras. Genes & Development, vol. 8, No. 3, pp. 1502-1513, 1994.*
Criqui-Filipe et al. Net, a negative Ras-switchable TCF, contains a second inhibition domain, the CID, that mediates repression through interactions with CtBP and de-acetylation. The EMBO Journal, vol. 18, No. 12, pp. 3392-3403, 1999.*
Sewalt et al. C-Terminal binding protein is a transcriptional repressor that interacts with a specifc class of vertebrate Polycomb proteins. Molecular and Cellular Biology, vol. 19, No. 1, pp. 777-787, Jan. 1999.*
Price et al. Comparative analysis of the ternary complex factors Elk-1, SAP-1a and SAP-2 (ERP/NET). The EMBO Journal. vol. 14, No. 11, pp. 2589-2601, Jun. 1995.*
Kaufman, RJ. DNA transfection to study translational control in mammalian cells. Methods: A companion to Methods in Enzymology, vol. 11, pp. 361-370, 1997.*
Inuzuka et al. Differential regulation of immediate early gene expression in preadipocyte cells through multiple signaling pathways. Biochemical and Biophysical Research Communications, vol. 265, pp. 664-668, 1999.*
Thuerauf et al. p38 Mitogen-activated protein kinase mediates the transcriptional induction of the atrial natriuretic factor gene through a serum response element. A potential role for the transcription factor ATF6. The Journal of Biological Chemistry, vol. 273, No. 32, pp. 20636-20643, Aug. 1998.*
Arbiser Jack L. et al., Oncogenic H-ras Stimulates Tumor Angiogenesis By Two Distinct Pathways, Proc. Nat'l. Acad. Sci. USA., (1997), vol. 94, pp. 861-866.
Ayadi A. et al., Net, An Ets Ternary Complex Transcription Factor, Is Expressed In Sites Of Vasculogenesis, Angiogenesis, And Chondrogenesis During Mouse Development, Mechanisms Of Development, (2001), vol. 102, pp. 205-208.
Boshoff Chris, Coupling Herpesvirus To Angiogenesis, Nature, (1998), vol. 391, pp. 24-25.
Brown Kathryn J. et al., A Novel In Vitro Assay For Human Angiogenesis, Laboratory Investigation, (1996), vol. 75, No. 4, pp. 539-555.
Dumont Daniel J. et al., Cardiovascular Failure In Mouse Embryos Deficient In VEGF Receptor-3, Science, (1998), vol. 282, pp. 946-949.
Evans S.M. et al., Imaging Hypoxia In Diseased Tissues, Advances In Experimental Medicine And Biology, (1997), vol. 428, pp. 595-603.
Maira Sauveur-Michel et al., Net (ERP/SAP2), One Of The Ras-Iducivle TCFs, Has A Novel Inhibitory Domain With Resemblance To The Helix-Loop-Helix Motif, The EMBO Journal, (1996), vol. 15, No. 21, pp. 5849-5865.
Price Mary Ann et al., Integration Of Growth Factor Signals At The c-fos Serum Response Element, Philosophical Transactions Of The Royal Society Of London B Biological, (1996), vol. 351, No. 1339, pp. 551-559.
Silverman Eric S. et al., Pathways Of Egr-1-Mediated Gene Transcription In Vascular Biology, American Journal Of Pathology, (1999), vol. 154, No. 3, pp. 665-670.
Yoshida A. et al., Intraocular Neovascularization, Histology & Histopathology, (1999), vol. 14, pp. 1287-1294.

* cited by examiner

*Primary Examiner*—Celine X Qian
*Assistant Examiner*—Jennifer Dunston

(57) ABSTRACT

The present invention relates to the regulation of the activity of NET (ERP/SAP-2) protein and to compounds which modify or regulate NET protein activity. The invention further relates to methods of screening for agonists or antagonists of NET in order to identify new pro-angiogenic or anti-angiogenic compounds and to therapeutic uses of these compounds. The invention also relates to transgenic animals bearing mutations in NET gene.

17 Claims, 25 Drawing Sheets a: GPCR
b: GPCR+Anti-VEGF-Ab
c: GPCR+AntiNet
d: GPCR+AntiNet+rhVEGF
e: GPCR+Transdominant Net
f: GPCR+Transdominant Net+rhVEGF

Net and Elk expression in GPCR-control and GPCR-antiNet clones

A pools

B clones

Tumor gnenerated by GPCR and PCR-AntiNet clones in nude mice

A: tumor of GPCR clone
B: tumor of GPCR-AntiNet clone
arrow: newly formed blood vessels induced by the tumor Vessel Density In Tumors Differences of Hypoxic Tension In Tumors B: GPCR-Vector A: GPCR-AntiNet Angiogenesis induced by rhFGF-b in cornea of mice Microvessel Formation In Mice Aortic Ring
Angiogenesis Assay

Figure 24a

Human Net 1   mesaitlwqf llqllldqkh ehlicwtsnd gefkllkaee vaklwglrkn ktnmnydkls
    ‾‾‾‾‾‾‾‾‾‾
    A box (ets domain), lwqfllqlll (NES)

61  ralryyydkn iikkvigqkf vykfvsfpei lkmdphavei sreslllqds dckvspegre
    ‾‾‾‾‾‾‾‾‾‾
    A box (ets domain), lwqfllqlll (NES)

121 ahkhglavlr stsrneyihs glyssftins lenppdafka ikrekleepp edsppveevr
    ‾‾‾‾‾‾‾‾‾‾               ‾‾‾‾‾‾‾‾‾‾‾‾‾‾‾‾‾‾‾‾‾‾‾‾‾‾‾‾‾‾‾‾‾‾‾‾‾‾‾‾
    B box (SRF interaction)   NID (Net inhibitory domain)

181 tvirfvtnkt dkhvtrpvvs lpstseaaaa saflassvsa kisslmlpna asissaspfs
                ‾‾‾‾‾‾‾‾‾‾‾‾‾‾‾‾‾‾‾‾‾‾‾‾‾‾‾‾‾‾ ‾‾‾‾‾‾‾‾‾‾‾‾‾‾‾‾‾‾‾‾‾
                NID (Net inhibitory domain)      JEK (JNK interaction and export
                                                 induced by phosphorylation)

241 srspslspks ppsehrslf leaachdsds leplnlssgs ktkspslppk akkpkgleis
               ‾‾‾‾‾‾‾‾‾‾‾‾‾‾‾‾‾‾‾ ‾‾‾‾‾‾‾‾‾‾ ‾‾‾‾‾‾‾‾‾‾ ‾‾‾‾‾‾‾‾‾‾
               JEK (JNK interaction and export  CID (CtBP interaction  D box (NLS and ERK1 +
               induced by phosphorylation)       domain)                p38 binding)

301 applvlsgtd igsialnspa lpsgsltpaf ftaqtpngll ltpsplissi hfwsslspva
                          ‾‾‾‾‾‾‾‾‾‾‾‾‾‾‾‾‾‾‾‾‾‾‾‾‾‾‾‾‾‾‾‾‾‾‾‾‾‾‾‾‾‾
                          C box (pylation induced transactivation)

361 plsparlqgp stlfgfptll nghmpvpips ldraaspvll ssnsqks
    ‾‾‾‾‾‾‾‾‾‾‾‾‾‾‾‾‾‾‾‾‾
    C box (Pylation induced transactivation)

Figure 24b

Mouse Net

1 <u>mesaitlwqf llhllldqkh ehlicwtsnd gefkllkaee vaklwglrkn ktnmnydkls</u>
  A box (ets domain), lwqfllqlll (NES)

61 <u>ralryyydkn iikkvigqkf vykfvsfpdi lkmdphavei sresllqdg dckvspegre</u>
  A box (ets domain), 121 vhrhglsslk <span style="border:1px solid">sasrneylhs glyssftins l</span>enapeafka iktekleepc ddsppveevr
  B box (SRF interaction)                    NID (Net inhibitory domain)

181 tvirfvtnkt dkhitrpvms lpststetaaa aasaflassv <span style="border:1px solid">sakisslmlp</span> naasvssvsp
  NID (Net inhibitory domain)                    JEX (JNK interaction and export
                                                 induced by phosphorylation)

241 sssrspslsp dsplpsehrs lfleaaches dsleplnlss gs<span style="border:1px solid">ktkspslp</span> <span style="border:1px solid">pkgkkpkgle</span>
  JEX (JNK interaction and export          CID (CtBP interaction      D box (NLS and ERK1
  induced by phosphorylation)              domain)                    + p38 binding)

301 i<span style="border:1px solid">sapqlllsg tdigsialns pa</span>lpsgsltp afftaqtpsg lflasspllp sihfwsslsp
  D box (NLS and ERK1              C box (Pylation induced transactivation)
  + p38 binding)

361 vaplsparlq gpntlfqfpt llnghmpvpl psldrapspv llspssqks
  C box (Pylation induced transactivation)

SEQUENCE LISTING

```
<160> NUMBER OF SEQ ID NOS: 15
<210> SEQ ID NO 1
<211> LENGTH: 1224
<212> TYPE: DNA
<213> ORGANISM: Homo sapiens

<400> SEQUENCE: 1
atggagagtg caatcacgct gtggcagttc ctgttgcagt tgctgctgga tcagaaacat      60
gagcatttga tctgctggac ctcgaacgat ggtgaattca agctcctcaa agcagaagaa     120
```

```
gtggccaagc tgtggggact ccgaaaaaac aaaacaaata tgaactatga taagctgagc      180
agagccctgc gatactatta tgacaagaac atcatcaaga aggtgatcgg gcagaagttt      240
gtgtacaagt ttgtctcttt cccggagatc ctgaagatgg atcctcacgc ggtggagatc      300
agccgggaga gccttctgct gcaggacagc gactgcaagg tgtctccgga gggccgcgag      360
gcccacaaac acggcctggc cgtcctcaga agcacgagcc gcaacgaata catccactca      420
ggcctgtact cgtccttcac cattaattcc ctggagaacc caccagacgc cttcaaggcc      480
atcaagaggg agaagctgga ggagccgccc aagacagcc ccccgtgga agaagtcagg       540 actgtgatca ggtttgtgac aataaaaacc gacaagcacg tcaccaggcc ggtggtgtcc      600
ctgccttcca cgtcagaggc tgcggcggcg tccgccttcc tggcctcgtc cgtctcggcc      660
aagatctcct ctttaatgtt gccaaacgct gccagtattt catccgcctc acccttctca      720
tctcggtccc cgtccctgtc ccccaagtca cccctcccct tgaacacag aagcctcttc       780 ctggaggccg cctgccatga ctccgattcc ctggagcccct tgaacctgtc atcgggctcc      840
aagaccaagt ctccatctct tcccccaaag gccaaaaaac ccaaaggctt ggaaatctca      900
gcgcccccgc tggtgctctc cggcaccgac atcggctcca tcgccctcaa cagcccagcc      960 ctccccctcgg gatccctcac cccagccttc ttcaccgcac agacaccaaa tggattgctt     1020
ctgactccga gtccactgct ctccagcata catttctgga gcagccttag tccagttgct     1080
ccgctgagtc ctgccaggct gcaagggcca agcacgctgt tccagttccc cacactgctt     1140
aatggccaca tgccagtgcc aatccccagt ctggacagag ctgcttctcc agtactgctt     1200
tcttcaaact ctcagaaatc ctga                                            1224

<210> SEQ ID NO 2
<211> LENGTH: 407
<212> TYPE: PRT
<213> ORGANISM: Homo sapiens

<400> SEQUENCE: 2

Met Glu Ser Ala Ile Thr Leu Trp Gln Phe Leu Leu Gln Leu Leu
1               5                   10                  15

Asp Gln Lys His Glu His Leu Ile Cys Trp Thr Ser Asn Asp Gly Glu
            20                  25                  30

Phe Lys Leu Leu Lys Ala Glu Glu Val Ala Lys Leu Trp Gly Leu Arg
        35                  40                  45

Lys Asn Lys Thr Asn Met Asn Tyr Asp Lys Leu Ser Arg Ala Leu Arg
    50                  55                  60

Tyr Tyr Tyr Asp Lys Asn Ile Ile Lys Lys Val Ile Gly Gln Lys Phe
65                  70                  75                  80

Val Tyr Lys Phe Val Ser Phe Pro Glu Ile Leu Lys Met Asp Pro His
                85                  90                  95

Ala Val Glu Ile Ser Arg Glu Ser Leu Leu Leu Gln Asp Ser Asp Cys
            100                 105                 110

Lys Val Ser Pro Glu Gly Arg Glu Ala His Lys His Gly Leu Ala Val
        115                 120                 125

Leu Arg Ser Thr Ser Arg Asn Glu Tyr Ile His Ser Gly Leu Tyr Ser
    130                 135                 140

Ser Phe Thr Ile Asn Ser Leu Glu Asn Pro Pro Asp Ala Phe Lys Ala
145                 150                 155                 160

Ile Lys Arg Glu Lys Leu Glu Glu Pro Pro Glu Asp Ser Pro Pro Val
                165                 170                 175
```

```
Glu Glu Val Arg Thr Val Ile Arg Phe Val Thr Asn Lys Thr Asp Lys
            180                 185                 190

His Val Thr Arg Pro Val Val Ser Leu Pro Ser Thr Glu Ala Ala
            195                 200                 205

Ala Ala Ser Ala Phe Leu Ala Ser Ser Val Ser Ala Lys Ile Ser Ser
        210                 215                 220

Leu Met Leu Pro Asn Ala Ala Ser Ile Ser Ser Ala Ser Pro Phe Ser
225                 230                 235                 240

Ser Arg Ser Pro Ser Leu Ser Pro Lys Ser Pro Leu Pro Ser Glu His
                245                 250                 255

Arg Ser Leu Phe Leu Glu Ala Ala Cys His Asp Ser Asp Ser Leu Glu
            260                 265                 270

Pro Leu Asn Leu Ser Ser Gly Ser Lys Thr Lys Ser Pro Ser Leu Pro
        275                 280                 285

Pro Lys Ala Lys Lys Pro Lys Gly Leu Glu Ile Ser Ala Pro Pro Leu
    290                 295                 300

Val Leu Ser Gly Thr Asp Ile Gly Ser Ile Ala Leu Asn Ser Pro Ala
305                 310                 315                 320

Leu Pro Ser Gly Ser Leu Thr Pro Ala Phe Phe Thr Ala Gln Thr Pro
                325                 330                 335

Asn Gly Leu Leu Leu Thr Pro Ser Pro Leu Leu Ser Ser Ile His Phe
            340                 345                 350

Trp Ser Ser Leu Ser Pro Val Ala Pro Leu Ser Pro Ala Arg Leu Gln
        355                 360                 365

Gly Pro Ser Thr Leu Phe Gln Phe Pro Thr Leu Leu Asn Gly His Met
    370                 375                 380

Pro Val Pro Ile Pro Ser Leu Asp Arg Ala Ala Ser Pro Val Leu Leu
385                 390                 395                 400

Ser Ser Asn Ser Gln Lys Ser
                405

<210> SEQ ID NO 3
<211> LENGTH: 1230
<212> TYPE: DNA
<213> ORGANISM: Mus musculus

<400> SEQUENCE: 3
atggagagtg caatcacgct gtggcagttc ctcttgcact tgctgctgga ccagaaacat    60
gagcacctca tctgctggac atcgaacgat ggcgagttca gctcctcaa ggcagaagaa    120 gtggccaagc tgtggggcct ccgcaagaac aagaccaaca tgaactacga caagctgagc    180
agagcgctga gatactatta cgacaagaac atcatcaaga aagtgatcgg cagaagtttt    240
gtgtacaagt tcgtctcttt cccggatatc ctgaaaatgg atcctcacgc ggtagagatc    300
agccgggaga gcctcctgct gcaggacggc gactgtaagg tgtccccgga aggccgagag    360
gtccacaggc acggcttgtc ctccctcaaa agtgccagcc gcaacgagta cctccactcg    420
gggctctact cgtccttcac catcaactcc ctggagaacg ctccagaggc cttcaaggcc    480
atcaagacgg agaagctgga ggagccctgt gatgacagcc ccctgtggga agaagtcagg    540
actgtgatca ggtttgtgac caataaaacc gacaagcaca tcaccaggcc tgtgatgtcc    600
ctgccttcca catccgagac cgctgcggca gcggcatccg cttttctggc ctcatctgtc    660
tcagccaaga tctcctcttt aatgttgcca aatgctgcca gcgtttcgtc tgtgtcaccc    720
tcttcatctc ggtccccatc cctgtccccc gactctcccc tcccttctga acacagaagc    780
```

-continued

```
ctcttcctgg aggcagcctg ccatgagtcg gattctctgg agcccctgaa tctgtcatcg      840
ggctccaaaa ccaagtctcc atctcttccc ccaaaaggca aaaaacccaa aggcttggaa      900
atctctgcac cccaactgtt gctctccggc accgacatcg gctccatcgc cctcaacagc      960
ccagccctcc cctcaggatc cctcactcca gccttcttca ccgcacagac accaagtgga     1020
ctgtttctgg cctcgagtcc gctgctgccc agcatacact tctggagcag ccttagtccg     1080
gtcgccccac tgagtcctgc caggctgcaa gggccgaaca cacttttcca gttccccaca     1140
ctgctcaacg gtcacatgcc ggtgccgctc cccagtctgg acagagctcc atccccagtt     1200
ctgctgtccc ccagctctca gaaatcctga                                     1230
```

<210> SEQ ID NO 4
<211> LENGTH: 409
<212> TYPE: PRT
<213> ORGANISM: Mus musculus

<400> SEQUENCE: 4

```
Met Glu Ser Ala Ile Thr Leu Trp Gln Phe Leu Leu His Leu Leu Leu
1               5                   10                  15

Asp Gln Lys His Glu His Leu Ile Cys Trp Thr Ser Asn Asp Gly Glu
            20                  25                  30

Phe Lys Leu Leu Lys Ala Glu Glu Val Ala Lys Leu Trp Gly Leu Arg
        35                  40                  45

Lys Asn Lys Thr Asn Met Asn Tyr Asp Lys Leu Ser Arg Ala Leu Arg
    50                  55                  60

Tyr Tyr Tyr Asp Lys Asn Ile Ile Lys Lys Val Ile Gly Gln Lys Phe
65                  70                  75                  80

Val Tyr Lys Phe Val Ser Phe Pro Asp Ile Leu Lys Met Asp Pro His
                85                  90                  95

Ala Val Glu Ile Ser Arg Glu Ser Leu Leu Leu Gln Asp Gly Asp Cys
            100                 105                 110

Lys Val Ser Pro Glu Gly Arg Glu Val His Arg His Gly Leu Ser Ser
        115                 120                 125

Leu Lys Ser Ala Ser Arg Asn Glu Tyr Leu His Ser Gly Leu Tyr Ser
    130                 135                 140

Ser Phe Thr Ile Asn Ser Leu Glu Asn Ala Pro Glu Ala Phe Lys Ala
145                 150                 155                 160

Ile Lys Thr Glu Lys Leu Glu Glu Pro Cys Asp Asp Ser Pro Pro Val
                165                 170                 175

Glu Glu Val Arg Thr Val Ile Arg Phe Val Thr Asn Lys Thr Asp Lys
            180                 185                 190

His Ile Thr Arg Pro Val Met Ser Leu Pro Ser Thr Ser Glu Thr Ala
        195                 200                 205

Ala Ala Ala Ser Ala Phe Leu Ala Ser Ser Val Ser Ala Lys Ile
    210                 215                 220

Ser Ser Leu Met Leu Pro Asn Ala Ala Ser Val Ser Ser Val Ser Pro
225                 230                 235                 240

Ser Ser Ser Arg Ser Pro Ser Leu Ser Pro Asp Ser Pro Leu Pro Ser
                245                 250                 255

Glu His Arg Ser Leu Phe Leu Glu Ala Ala Cys His Glu Ser Asp Ser
            260                 265                 270

Leu Glu Pro Leu Asn Leu Ser Ser Gly Ser Lys Thr Lys Ser Pro Ser
        275                 280                 285
```

```
Leu Pro Pro Lys Gly Lys Pro Lys Gly Leu Glu Ile Ser Ala Pro
    290                 295                 300

Gln Leu Leu Leu Ser Gly Thr Asp Ile Gly Ser Ile Ala Leu Asn Ser
305                 310                 315                 320

Pro Ala Leu Pro Ser Gly Ser Leu Thr Pro Ala Phe Phe Thr Ala Gln
                325                 330                 335

Thr Pro Ser Gly Leu Phe Leu Ala Ser Ser Pro Leu Leu Pro Ser Ile
            340                 345                 350

His Phe Trp Ser Ser Leu Ser Pro Val Ala Pro Leu Ser Pro Ala Arg
        355                 360                 365

Leu Gln Gly Pro Asn Thr Leu Phe Gln Phe Pro Thr Leu Leu Asn Gly
    370                 375                 380

His Met Pro Val Pro Leu Pro Ser Leu Asp Arg Ala Pro Ser Pro Val
385                 390                 395                 400

Leu Leu Ser Pro Ser Ser Gln Lys Ser
                405
```

```
<210> SEQ ID NO 5
<211> LENGTH: 25
<212> TYPE: DNA
<213> ORGANISM: Artificial
<220> FEATURE:
<223> OTHER INFORMATION: Synthetic Primer Sequence UC54

<400> SEQUENCE: 5
tgaaacgtgt aatccttgtg tcctc                                          25

<210> SEQ ID NO 6
<211> LENGTH: 25
<212> TYPE: DNA
<213> ORGANISM: Artificial
<220> FEATURE:
<223> OTHER INFORMATION: Synthetic Primer Sequence UC56

<400> SEQUENCE: 6
taatttccaa gttctcggca cgtag                                          25

<210> SEQ ID NO 7
<211> LENGTH: 25
<212> TYPE: DNA
<213> ORGANISM: Artificial
<220> FEATURE:
<223> OTHER INFORMATION: Synthetic Primer Sequence UC57

<400> SEQUENCE: 7
gaccgcttcc tcgtgcttta cggta                                          25

<210> SEQ ID NO 8
<211> LENGTH: 24
<212> TYPE: DNA
<213> ORGANISM: Artificial
<220> FEATURE:
<223> OTHER INFORMATION: Synthetic Primer Sequence EX1

<400> SEQUENCE: 8
ctagaaatct ccccaagaag actc                                           24

<210> SEQ ID NO 9
<211> LENGTH: 24
<212> TYPE: DNA
<213> ORGANISM: Artificial
<220> FEATURE:
<223> OTHER INFORMATION: Synthetic Primer Sequence EX2a
```

```
<400> SEQUENCE: 9
gttgtcgtca tagtatctca gcgc                                          24

<210> SEQ ID NO 10
<211> LENGTH: 24
<212> TYPE: DNA
<213> ORGANISM: Artificial
<220> FEATURE:
<223> OTHER INFORMATION: Synthetic Primer Sequence EX2b

<400> SEQUENCE: 10
tgctggacat cgaacgatgg cgag                                          24

<210> SEQ ID NO 11
<211> LENGTH: 24
<212> TYPE: DNA
<213> ORGANISM: Artificial
<220> FEATURE:
<223> OTHER INFORMATION: Synthetic Primer Sequence EX3a

<400> SEQUENCE: 11
acttgtacac aaacttctgc ccga                                          24

<210> SEQ ID NO 12
<211> LENGTH: 24
<212> TYPE: DNA
<213> ORGANISM: Artificial
<220> FEATURE:
<223> OTHER INFORMATION: Synthetic Primer Sequence EX3b

<400> SEQUENCE: 12
ctagaaatct ccccaagaag actc                                          24

<210> SEQ ID NO 13
<211> LENGTH: 24
<212> TYPE: DNA
<213> ORGANISM: Artificial
<220> FEATURE:
<223> OTHER INFORMATION: Synthetic Sequence EX4

<400> SEQUENCE: 13
tcgaggccag aaacagtcca cttg                                          24

<210> SEQ ID NO 14
<211> LENGTH: 21
<212> TYPE: DNA
<213> ORGANISM: Artificial
<220> FEATURE:
<223> OTHER INFORMATION: Synthetic Oligonucleotide derived from SRE
      Sequence

<400> SEQUENCE: 14
tcgagccgga agtgacgtcg a                                             21

<210> SEQ ID NO 15
<211> LENGTH: 25
<212> TYPE: DNA
<213> ORGANISM: Artificial
<220> FEATURE:
<223> OTHER INFORMATION: SRE Sequence

<400> SEQUENCE: 15
tacacaggat gtccatatta ggaca                                         25
```

NET, A TRANSCRIPTION FACTOR OF THE TCF FAMILY, AS REGULATOR OF ANGIOGENIC FACTOR EXPRESSION

FIELD OF THE INVENTION

The present invention relates to the regulation of the activity of NET (ERP/SAP-2) protein and to compounds which modify or regulate NET protein activity. The invention further relates to methods of screening for agonists or antagonists of NET in order to identify new pro-angiogenic or anti-angiogenic compounds and to therapeutic uses of these compounds. The invention also relates to transgenic animals bearing mutations in NET gene.

BACKGROUND OF THE INVENTION

In mammalian cells, TCF (Ternary Complex Factor) transcription factors belongs to the ets 1 family. They share through their ets DNA-binding domain (85 amino acids) the ability to bind to the Serum Responsive Element (SRE) when associated to SRF dimers (Serum Response factor). The ternary complex formation requires the presence of a SRE consensus sequence SEQ ID No: 17 (C/A)(C/A)GGA(A/T) next to a SRF consensus site SEQ ID No: 16 (CC(A/T)6GG) without any orientation requirement. The neighbouring of these two sequences in several immediate-early gene promoters induces their transcription in response to mitogens as serum or growth factors but also in response to phorbol esters and stress stimuli. These sequences were first identified in the c-fos promoter on which Ets proteins and SRF are constitutively bound.

Known members of the TCF family members are Elk-1, SAP-1 and Net (SAP-2, ERP). These proteins are widely expressed.

This sub-family of TCF transcription factors is defined by a strong sequence homology pattern that relates to the presence of different functional domains. Starting from amino to carboxy terminal, the members of the TCF family display at least four homology boxes in their polypeptidic sequence:
- the A-box also called the ETS DNA-binding domain that is directly involved in binding with the SRE consensus sequence,
- the B-box (a short hydrophilic region) is involved in interaction with SRF,
- the D-box located upstream to the C-box consists in a MAPK targetting domain,
- the C-box and C-terminal sequences contain the phosphorylation sites (six to seven (S/T)P motifs) by MAPKinases (ERKs, JNKs and p38s) and consists in a transcriptional activation domain. The induction of transcriptional activity by TCF requires phosphorylation of the TCF by MAPKs in this regulatory domain.

The position of A, B, C and D boxes with regards to amino acid sequence of human or murine polypeptide is as follows: A (human)=1-90, B (human)=133-151, C (human)=321-378, D (human)=290-299 ; A (murine)=1-90, B (murine)=133-151, C (murine)=323-380, D (murine)=291-301.

The formation of the ternary TCF-SRF-SRE complex requires at the same time protein/DNA binding (TCF to SRE and SRF to SRF consensus sequence) and the protein/protein interaction between the TCF B-box and SRF. This complex assembly is facilitated by TCF phosphorylation by MAPKs.

Murine Net was cloned in 1994 by Giovane et al. (Genes Dev., 8, 1502-1513 (1994)) and was also reported by T. Liberman et al. (ERP a new member of the ets transcription factor/oncoprotein family: cloning, characterization and differential expression during B-lymphocyte development. *Mol. Cell Biol.* 1994, 14: 3292-309) (ERP)( Accession number L19953). The human sequence is referred as Z36715 and the murine sequence is referred as Z32815 in GENBANK® (sequence database). Chromosomal localization of murine net gene was mapped to 10C-D1 and its human counterpart on 12q22-23. This last locus is now called ELK3. This localization corresponds to the sap2 gene. The Jackson laboratory and HGMW approved that elk3 is now the common loci for net/erp (murine) and its human match sap-2 (human) loci (Giovane et al. Locations of the est subfamily members of net, elk 1, and sap1 (ELK3, ELK1, and ELK4) on three homologous regions of the mouse and human genomes. Genomics (1995) 29:769-72).

Net in a normal cell context displays repressor activity on transcription. This can be interpreted through a competition for both MAPK phosphorylation and TCF formation. Net antisense stimulates SRE activity when stimulated by serum. The hypothesis of competition at phosphorylation site is validated by the negligible DNA-binding activity of Net protein at the c-fos SRE. A repressive activity on TCF-dependent transcription was also recently described for bHLH transcription factors through a competitive mechanism involving their ETS-domain binding Yates et al. (Id helix-loop-helix proteins inhibit nucleoprotein complex formation by the TCF ETS-domain transcription factors. EMBO J. (1999) 18: 968-76.)

Amongst the TCFs, Net has the particularity to possess also a NID Novel Inhibitory Domain located between aa 153-208, which contains a Helix-Loop-Helix protein-protein interaction motif. This NID inhibits specific DNA binding by Net but also transactivation in the absence of an activated ras signaling (Maira et al. Net (ERP/SAP2) one of the Ras inductible TCFs, has a novel inhibitory domain with resemblance to the helix-loop-helix motif. EMBO J. (1996) 15: 5849-65). Net has also a second inhibitory domain, the CID, aa 274-282, that interacts with CtBP (Criqui-Filipe et al. Net, a negative Ras switchable TCF, contains a second inhibitory domain, the CID, that mediates repression through interactions with CtBP and de-acetylation. EMBO J. (1999) 18 :3392-3403).

The Net C domain integrates the signalling from a range of activators of the MAPK cascades at different MAPK consensus phosphorylation sites (T/S-P). Depending on the nature of this activator, the transcriptional potential of Net is regulated by its subcellular translocation. Net sequence contains a nuclear localization signal (NLS) in the D box and a nuclear export signal (NES) in the Ets DNA binding domain. C. Ducret et al. (the Net repressor is regulated by nuclear export in response to anisomycin, UV and heat shocks M.C.B, 19: 7076-7087) have shown that the JNK pathway induces an active nuclear export of the Net protein. This effect is inhibited by leptomycin B that inhibits the NES binding to CRM1, required for this active nuclear export. The presence of this active NES is specific for Net sequence. Thus, JNKs are involved in Net phosphorylation but this activation doesn't result in transcriptional activation due to this cytoplasmic shuffling. JNK induces nuclear-cytoplasmic shuffling by phosphorylation of the JEX box (aa 233-253). In contrast, transcription activation involves phosphorylation of the C box by p38 and ERK1-2 (Ras) pathway (Ducret et al. Oncogene, in press).

Net transcriptional activity can be activated by oncogenic Ras, Src and Mos but not by an oncogenic Raf, thus showing that ERKs should not be directly involved in Net transactivation.

There is a need in the art to better understand the molecular mechanisms of NET in cellular processes. In particular, there is a need in the art to identify additional NET functions and/or interaction with cellular components. The present invention addresses this need, as discussed below.

The citation of any reference herein should not be construed as an admission that such reference is available as "Prior Art" to the instant application.

SUMMARY OF THE INVENTION

As noted above, the present invention concerns identification of novel functions of the Net transcription factor. Most unexpectedly the applicants have now shown that NET is involved in angiogenesis and that Net gene mutation in mammals affects the vascular system. Applicants have now evidenced that under normal condition NET is a repressor of angiogenesis. Applicants have also shown that NET can be activated through phosphorylation of specific Ser residues and they have discovered that activated NET promotes angiogenesis. Angiogenesis mediated by activated NET involves secretion of VEGF, and in context in which Net is activated, down regulation of NET reduces VEGF secretion and reduces angiogenesis. Moreover, it was shown that in context in which Net is activated, down regulation of NET inhibits tumour formation and leads to hypoxic tumors.

These findings designate NET as a key intermediate in regulation of angiogenesis. Down regulation of NET in a normal context increases angiogenesis whereas down regulation of NET in a pathological context or in a context in which NET is activated leads to a decrease of angiogenesis. This discovery provides an avenue for new therapeutic approaches in the regulation of angiogenesis thought modulation of Net activity. This discovery also provides new model systems for studying angiogenesis and diseases involving angiogenic disorders, it also provides for new screening methods for identifying compounds useful for the prevention or the treatment of these diseases.

Therefore, a first aspect of the invention provides for the use of all or part of NET polypeptide in a method for identifying compounds which modulate angiogenesis or which are effective for preventing and/or treating pathologies related with angiogenic disorders. Alternatively, the invention provides for the use of cells expressing all or part of NET polypeptide in such method. In a specific embodiment NET polypeptide is selected from the group consisting of a protein having the amino acid sequence depicted in SEQ ID NO:2, an allelic variant of the protein having the amino acid sequence depicted in SEQ ID NO:2, a splice variant of the protein having the amino acid sequence depicted in SEQ ID NO:2, and a homologous protein from another species of the protein having the amino acid sequence depicted in SEQ ID NO:2. In another embodiment part of the NET polypeptide used in the method comprises NET fragment selected from fragment corresponding to A box (human)=aa 1-90, B box (human)=aa 133-151, C box (human)=aa 321-378, D box (human)=aa 290-299. NID domain (human)=aa 153-308; JEX domain (human)=aa 233-353; CID domain (human) aa 274-282; A box (murine)=aa 1-90, B box (murine)=aa 133-151, C box (murine)=aa 323-380, D box (murine)=aa 291-301; NID domain (murine)=aa 155-197; JEX domain (murine)=aa 222-253; CID domain (murine)=aa 275-220. The murine NET polypeptide sequence is provided in SEQ ID No 4.

The method of identifying compounds can comprises detecting modulation of the transcription activity of NET or detecting modulation of NET/DNA interaction or modulation of NET phosphorylation or assessing ability of all or fragment of NET polypeptide to interact with other polypeptide element.

In a preferred embodiment, the compound is an antagonist of NET and the compound can be used for prevention and/or treatment of pathologies related or associated with angiogenic disorders such as Kaposi sarcoma, tumor growth, and/or other pathologies in which NET is activated. The pathologies related with angiogenic disorders include cancers and solid tumors for which antagonist of NET will act as antiangiogenic compound (in a context in which Net is activated) and will lead to prevention, reduction or regression of tumor growth.

In another preferred embodiment, the compound is a modulator of NET (either an agonist or an antagonist) and the compound can be used for prevention and/or treatment of pathologies related with angiogenic disorders in a context in which NET is not activated (or in a context in which cells are not transformed). Such pathologies may involve insufficient vascularization and require increase of angiogenesis. Such pathologies may also involve increased vascularization and require inhibition of angiogenesis.

As noted above, Net is an important factor for the regulation of angiogenesis. The present invention advantageously provides a method of screening for molecules that modulate the activity of Net, and thus angiogenesis. Any of the screening methods in the art can be used, particularly high through-put screening. Accordingly, the invention provides for a method for identifying compounds which modulate angiogenesis, said method comprising (i) providing a composition comprising a mammalian NET transcription factor, (ii) contacting the composition with the candidate compound, and, (iii), assessing the ability of said candidate compound to modulate NET function. The composition of the method can be a cell or a cellular extract or semi-purified extract or purified NET polypeptide. In a specific embodiment, the assessment step comprises detecting modulation of the transcription activity of NET, such as detecting a change in the level of expression of a reporter gene expressed under control of a chimeric protein consisting of the NET transactivation domain and a DNA binding domain of a transcription factor (such as GAL4 DNA binding domain). The detection of expression can be done in transiently or stably transfected mammalian cell. In another embodiment, assessment step comprises detecting modulation of NET/DNA interaction, for example by using gel shift assay or quantitation of labelled nucleotide bound to NET protein. In still another embodiment, the assessement step comprises detecting modulation of NET phosphorylation. The detection of modulation of Net phosphorylation can comprise determining NET phosphorylation as a result of kinase activity. The kinase can be p38α, p38β, ERK1, ERK2, JNK1, JNK2 or JNK3. In a further embodiment, assessement step comprises assessing ability of all or fragment of the NET polypeptide to interact with other polypeptidic elements, such as assessing the ability of NET SRF binding domain to interact with the SRE element or assessing ability of NET CtBP binding domain (CID domain) to interact with CtBP element or assessing both. Screening methods of the invention permit identification of a Net agonist or antagonist.

Yet another aspect of the invention, provides for a transgenic non-human animal comprising a mutation in NET gene. In a specific embodiment, the mutation is a deletion. In a preferred embodiment, the deletion leads to alternatively spliced NET mRNA lacking exon 2. The mutation may affects one allele or both alleles. In a specific embodiment, the animal is a rodent and preferably a mouse.

The transgenic animals according to the invention provides model systems for studying pathologies related to angiogenic disorders and for screening and/or testing compounds useful for the prevention and/or the treatment of these diseases. Organs from the transgenic animals (such as retina, aortas, etc.) are also useful for screening and/or testing such compounds.

Therefore, another aspect of the invention provides a method of determining the ability of a compound to modulate angiogenesis. Alternatively, the invention provides methods of identifying a compound effective for preventing and/or for treating pathologies related with angiogenic disorders. Preferred method comprises administering said compound to a transgenic animal comprising a mutation in NET gene and comparing angiogenesis to that in untreated control animal.

In another aspect, the invention provides for a compound capable of modulating angiogenesis. In a specific embodiment, the modulation of angiogenesis occurs through binding or interaction or competition with NET transcription factor. In another specific embodiment, the compound is capable of binding or interacting specifically with activated NET transcription factor (i.e. with phosphorylated NET). With this regards, inventors have now determined that activation of Net involves one or more of at least 6 Ser/Thr phosphorylated motifs (S/T-P motifs) at position 329, 337, 359, 365, 398, 403 of mouse sequence and at position 327, 335, 357, 363, 396, 401 of human sequence. Phosphorylation at position 359 and 365 (mouse) or phosphorylation at position 357 and 363 (human) are more particularly important for activation of Net. In yet another embodiment, the compound can modulate angiogenesis through regulation of any specific event upstream to Net phosphorylation.

The compound of the invention can be an antisense nucleic acid capable of down regulating or blocking expression of a NET gene. In another embodiment, the compound of the invention can be an intracellular binding protein. Yet in another embodiment, the compound of the invention can be a NET dominant-negative mutant.

In still another aspect, the invention provides a method for modulating NET expression in a cell by administering to the cell a compound capable of modulating NET levels and or biological activity of NET within the cell. In a preferred aspect of the invention, the cells are the cells of a patient, suffering from a pathology related to any angiogenic disorder, and the method comprises administering to the cells of a patient a compound capable of modulating angiogenesis. In a specific embodiment, the modulation of NET level or activity occurs through binding or interaction or competition with NET transcription factor. The compound can be a small molecule, an antisense nucleic acid capable of down-regulating or blocking expression of a NET gene, an intracellular binding protein or a NET dominant-negative mutant. The compound can be a small molecule or a polypeptide whose interaction with NET prevent NET transcription factor to reach nuclear localization.

In another aspect, the invention provides for the application of a compound capable to modulate NET activity or a pharmaceutically acceptable salt of such compound to the preparation of medicinal product intended for the prevention or the treatment of pathologies associated with angiogenic disorders. The compound can be a NET agonist or antagonist.

In a further embodiment, the invention provides a method of decreasing angiogenesis in a tissue in a normal context (i.e. in which NET is not activated) comprising increasing the level of NET protein in the cell. The NET protein can be a murine NET, and more preferably is a human NET. In a preferred embodiment, the cell has been transfected with a vector encoding NET under conditions permitting expression of the NET protein.

Alternatively, where desired, the invention provides a method of increasing angiogenesis in a tissue in a normal context (i.e. NET is not activated) comprising decreasing the level of NET protein in the cell or decreasing the activity of NET protein in the cell. The level of NET protein can be decreased by introducing a NET antisense nucleic acid into the cell, which antisense nucleic acid hybridizes under intracellular conditions to a NET mRNA. Alternatively, the activity of the NET protein can be decreased by introducing a single chain Fv antibody (scFv) that specifically binds NET into the cell at a level sufficient to bind to and inactivate NET.

In yet a further embodiment, and more preferably in a context in which NET is activated, the invention provides for a method of decreasing angiogenesis in a tissue comprising decreasing the level of NET protein in the cell or decreasing the activity of NET protein in the cell. The level of NET protein can be decreased by introducing a NET antisense nucleic acid into the cell, which antisense nucleic acid hybridizes under intracellular conditions to a NET mRNA. Alternatively, the activity of the NET protein can be decreased by introducing a single chain Fv antibody (scFv) that specifically binds NET into the cell at a level sufficient to bind to and inactivate NET.

These and other objects are addressed by this invention, which is explained in greater detail in the attached drawings and the following Detailed Description and Examples.

(A) Schematic representation of the wild type Net allele, the targeting vector and recombinant mutant Net allele. The deleted exon 2 contains the initiation translation codon and encodes amino acids 1-69 in the DNA binding domain of the Net protein. The position of the 3' probe used for Southern blot analysis is shown, as well as the XbaI-digested fragments of 13 Kb (wild-type) and 5 kb (mutant allele); B, BamHI; X, XbaI.

(B) Southern blot analysis of XbaI-digested DNA from the progeny from a heterozygous (±) intercross. Hybridisation using the 3' probe yielded bands corresponding to fragments of 13 kb for the wild-type allele (WT) or 5 kb for the targeted allele (M).

(C) PCR analysis of the same progeny. The genotype are indicated on the top, the arrows depict the specific amplification products for the wild-type (WT, 1550 bp) and the targeted allele (M, 1300 bp). The PCR primer set (UC54, UC56, UC57) are indicated in the targeting scheme.

(D) Detection of Net transcripts by RT-PCR RNA isolated from E16 wild-type and homozygous mutant embryos was used for RT-PCR reactions with primers from different exons of Net gene (exon1 to exon4). The RT-PCR primer sets are indicated on the left part of the panel. As expected with the deletion of exon 2, no amplification is seen in mutant (−/−) RNA with ex1/ex2 or ex2/ex3 sets. However an amplification product is observed between exon 3 and exon 4 (ex3/ex4 set) in the mutant as in the wild-type embryo. The RT-PCR reaction between exon1 and exon 3 (ex1/ex3 set) shows that a smaller product (90 bp) exists in the homozygous mutant embryo compared to the wild-type (217 bp).

(E) Western blot analysis of lung protein extracts from 2 weeks old wild-type, heterozygous and homozygous mice. The amount of the 49-kDA Net protein decreases in the heterozygous (±), to fully disappear in the homozygous mutant animal (−/−). However a new 42-kDA protein band appears in the mutant extract (as with the heterozygous).

Figure 15:
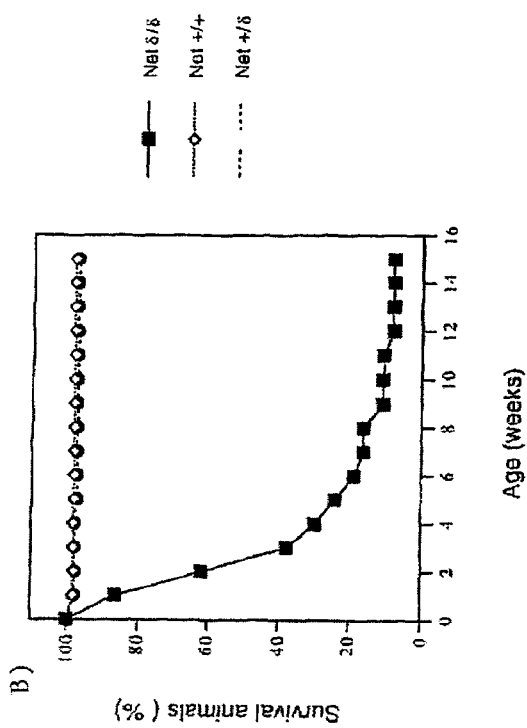
Figure 15:

FIG. 15: Phenotype of Net δ/δ mice. (A, B) Survival of Net δ/δ mice compared to the wild-type and heterozygous (+/δ) animals. (C) Representative picture of the phenotype developed by the Net δ/δ mice. This animal showed signs of respiratory distress at 6 days post-natally and died 2 days later. The thoracic cavity was found full of a milky liquid, typical of chylous effusion.

Figure 16:
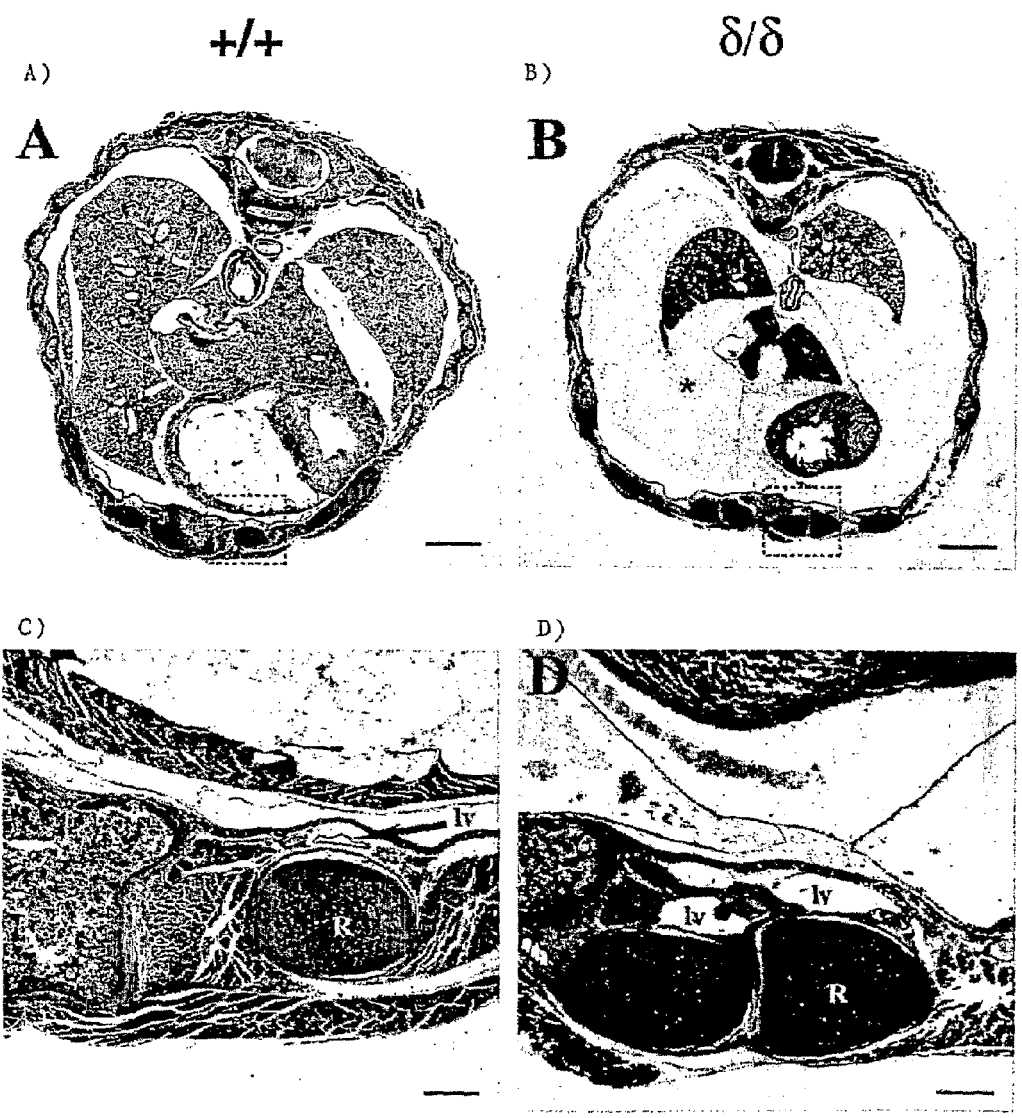

FIG. 16: Histological analysis of the Net δ/δ thorax cavity. Hematoxylin-eosin stained cross-sections of a wild-type (A) and mutant mouse thorax (B) are shown. Bar=0.8 mm. The respiratory distress symptoms were observed at 8 days of age for the Net δ/δ mouse, which was sacrified for this histological studies with a littermate Net +/+ mouse as control. The pleural space is clearly expanded in the mutant, filled by the chylous effusion (star). Note the compression of the lungs and heart by the accumulation of this effusion. Photographs (C) and (D) are magnifications of the dashed squares drawn in (A) and (B), respectively. The thoracic wall of Net δ/δ mouse (D) has dilated lymphatic vessels compare to the control (C). R, rib; lv, lymphatic vessel. Bar=0,2 mm.

Figure 17:
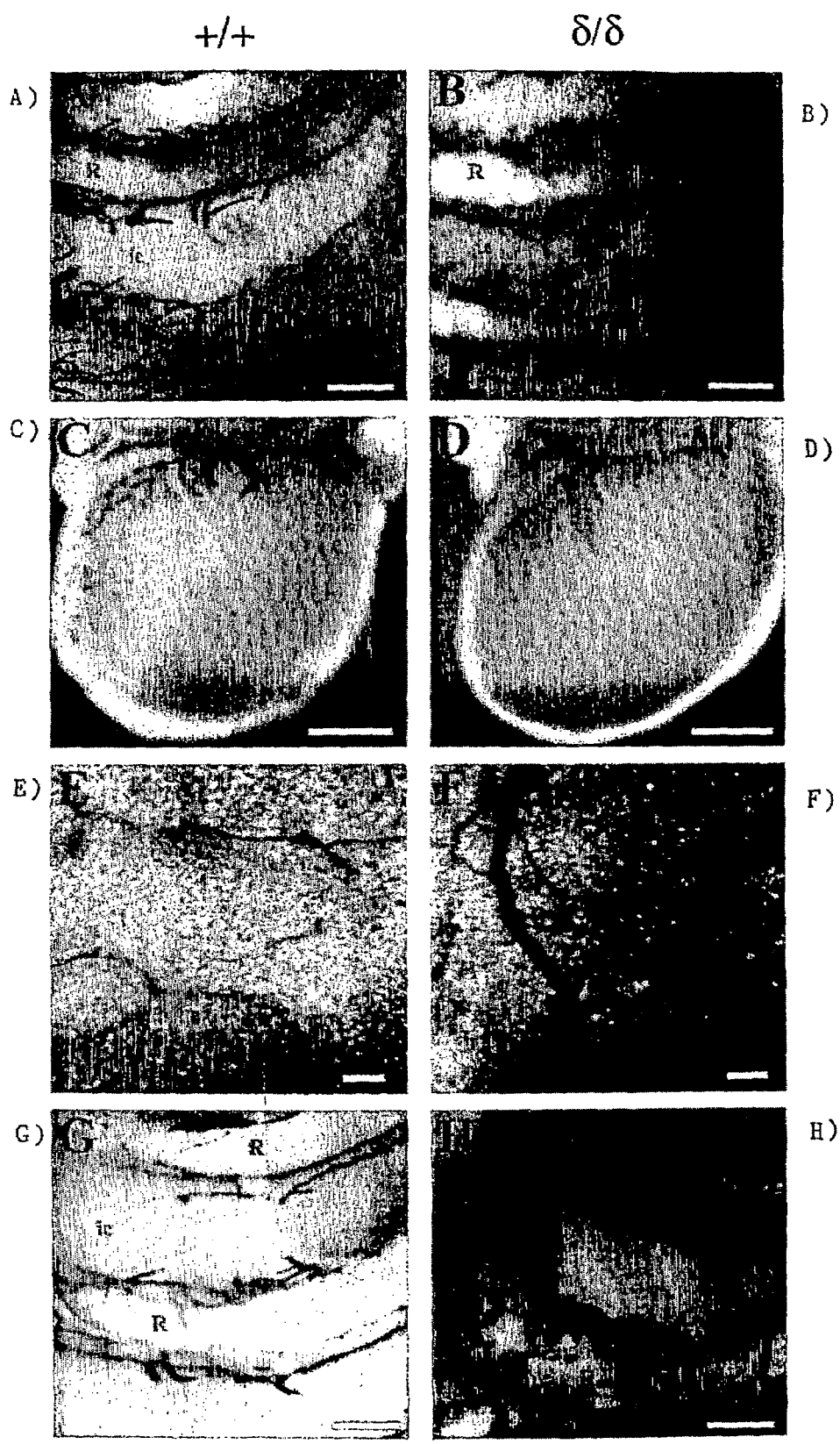

FIG. 17: Dilatation of the thoracic lymphatic vessels in Net δ/δ mice. Lymphatic vessels of Net +/+, VEGFR3 +/− (A, C, E, G) and Net δ/δ, VEGFR3 +/− mice (B, D, F, H), are visualised by X-Gal staining. (B, D and F) A Net δ/δ mouse that developed chylothorax at 10 days of age. The lymphatics of the mutant thoracic wall (B) are dilated compared to the littermate control (A). Bars=90 ?m. The pericardiac (C and D) and chest skin (E and F) lymph vessels in the same animals are not altered in the Net δ/δ mice (Bars=42 μm). In a 5 days-old mice, before the onset of the pleural effusion, the thoracic lymphatic vessels are already dilated in the Net δ/δ (H) compared to the littermate control (G). R, ribs; ic, intercostal region. (Bars=90 μm). Bars=90 ?m. The pericardiac (C and D) and chest skin (E and F) lymph vessels in the same animals are not altered in the Net δ/δ mice (Bars=42 μm). In a 5 days-old mice, before the onset of the pleural effusion, the thoracic lymphatic vessels are already dilated in the Net δ/δ (H) compared to the littermate control (G). R, ribs; ic, intercostal region. (Bars=90 μm).

Figure 18:
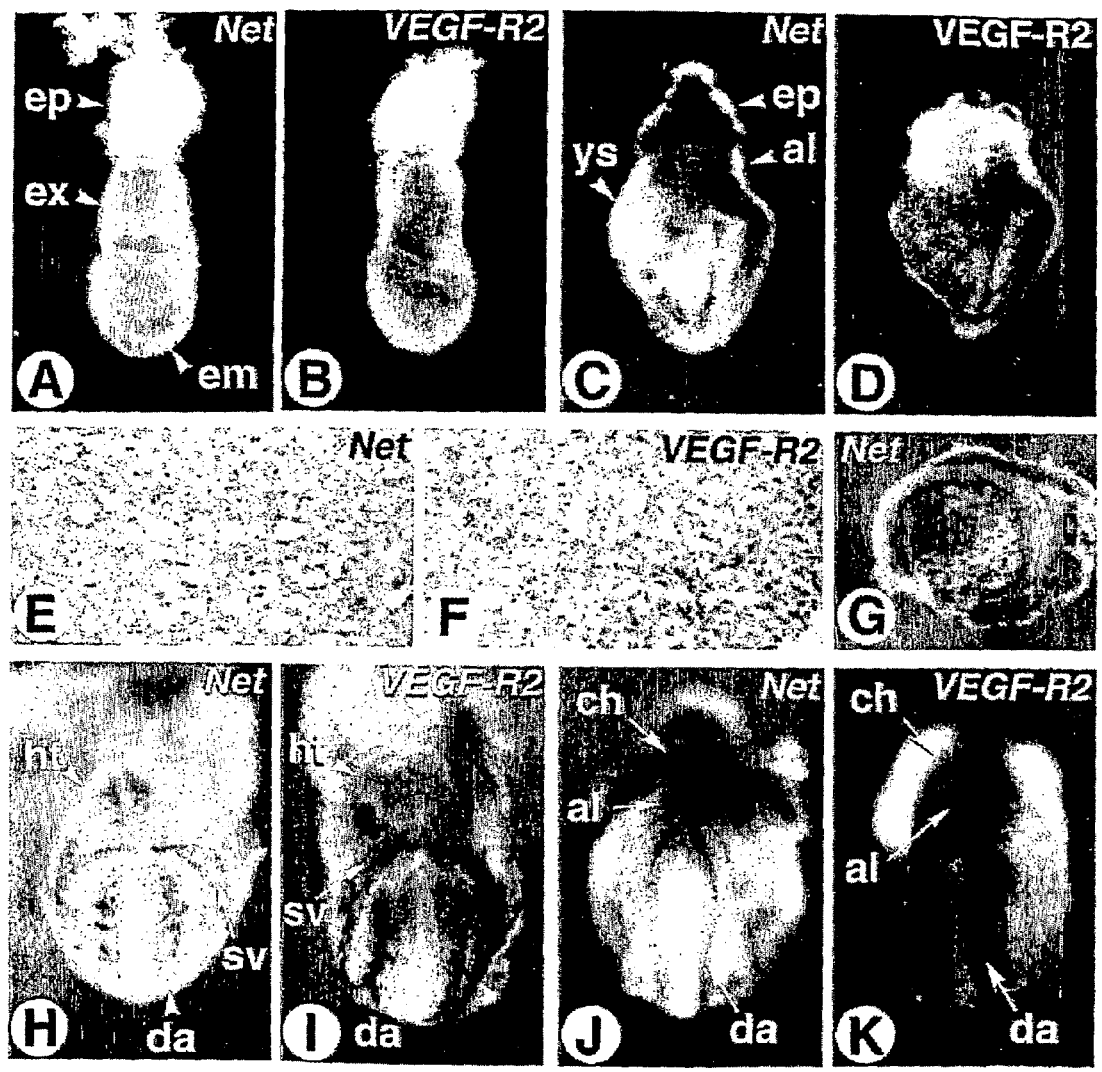

FIG. 18: Detection by whole-mount in situ hybridization of Net (A, C, E, G, H, and J), and VEGF-R2 (B, D, F, I and A) mRNA expression in E7.5 and E8.5 staged embryos. (A, B) E7.5 embryos. (C, D) Lateral views of E8.5 embryos in their yolk sac. (E, F) Expression in the dissected yolk sac of the E8.5 embryos. (G) Net expression within the inner surface of the dissected ectoplacental cone. (H, I) Anterior and (J, K) posterior views of the labelling observed in E8.5 staged embryos. Abbreviations: al, allantois; ch, chorion; da, dorsal aortae; em, embryonic tissue; ep, ectoplacental cone; ex, extra-embryonic tissue; ht, heart; sv, sinus venosus; ys, yolk sac.

Figure 19:
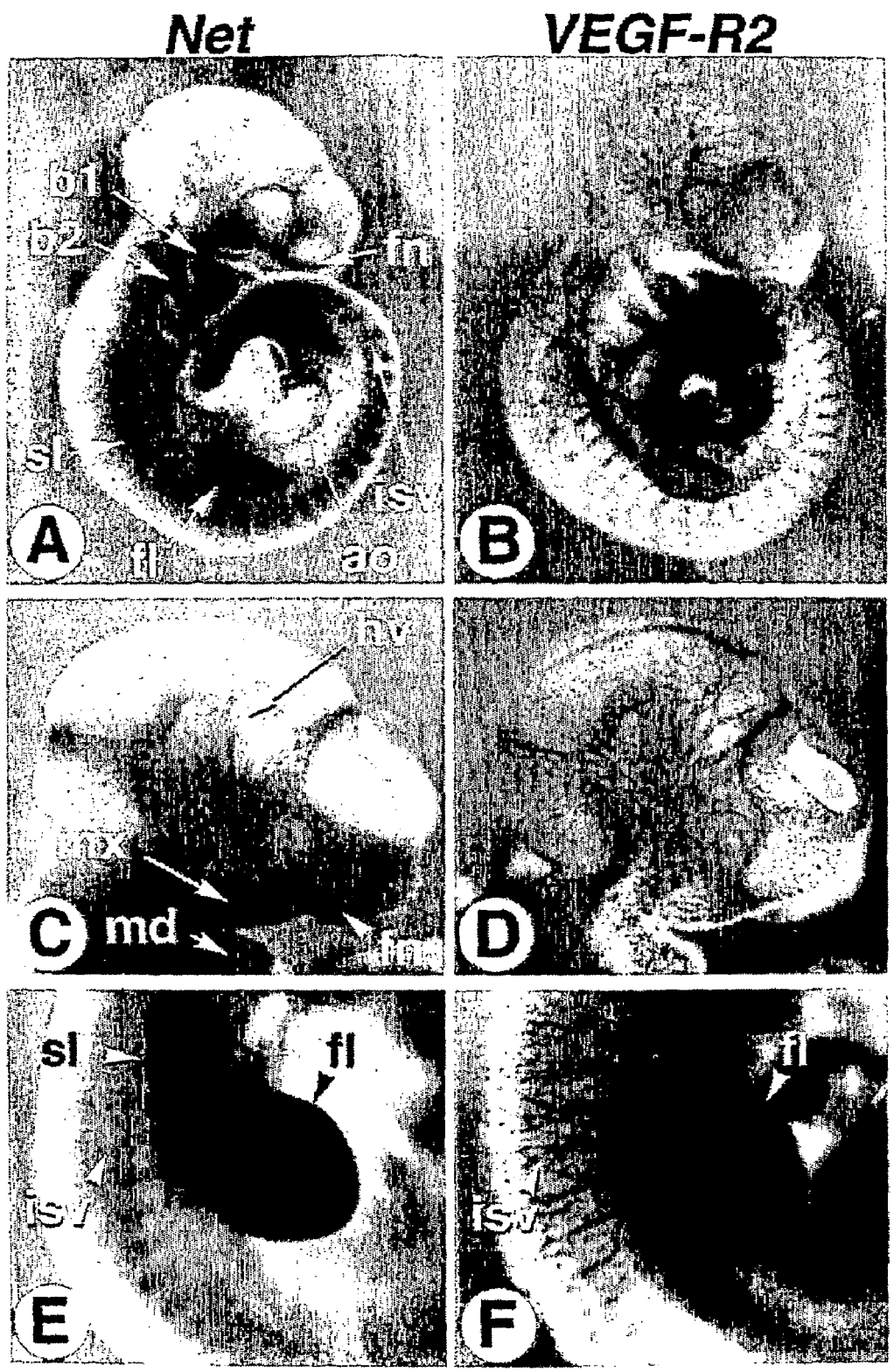

FIG. 19: Whole-mount mRNA detection of Net (A, C and E) and YEGF-R2 (B, D and F) transcripts at E9.5 and E10.5. (A, B) Lateral views of E9.5 embyos. (C, D) Expression in the head region from E10.5 embryos. (E, F) Lateral views of the trunk region from E10.5 staged embryos. Abbreviations: ao, aortae; b, branchial arches; fl, forelimb; fh, frontonasal mass; hv, head vessels; isv, intersomitic vessels; md, mandibular process; mx, maxillary process; sl, sclerotome; uv, umbilical vein.

Figure 20:
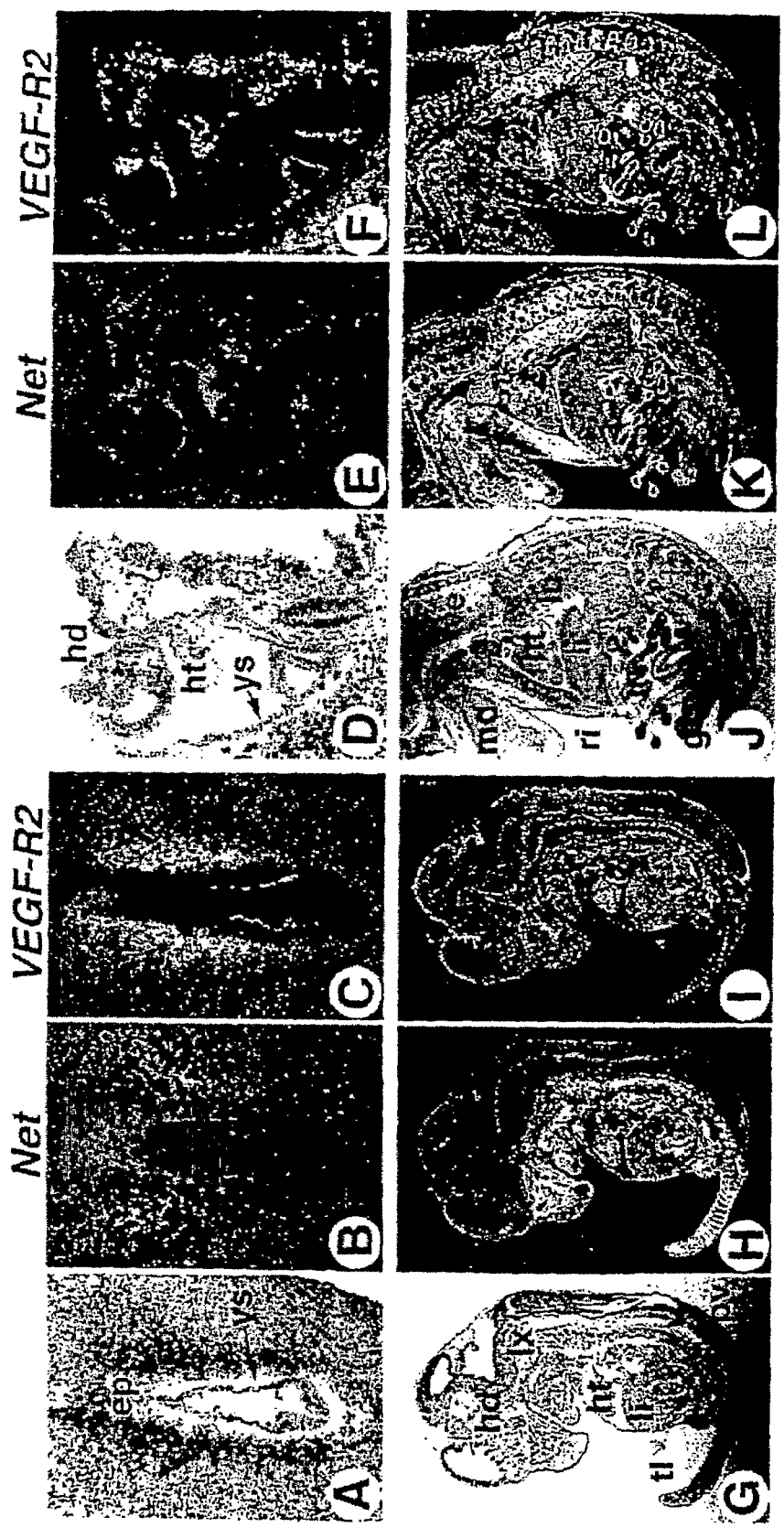

FIG. 20: Comparative analysis of Net and VEGF-R2 expression by in situ hybrisation at E7.5, E8.5, E12.5, and E14.5 stages. Consecutive frozen sections has been hybridized as indicated on pictures, by Net and VEGF-R2 probes. Each row of stages represented here, contains a bright-field view to show the histology (same for the FIG. 4). (A-C) and (D-F) represent sections through E7.5 and E8.5 embryo respectively, located in the maternal decidua. (G-I) and (J-L) show sagittal sections through an E12.5 and E14.5 embryos respectively. Abbreviations: ad, adrenal gland; ep, ectoplacental cone; gt, genital tubule; hd, head; ht, heart; in, intestine; ri, ribs; li, liver; 1×, larynx; md mandible; tl, tail; ys, yolk sac.

Figure 21:
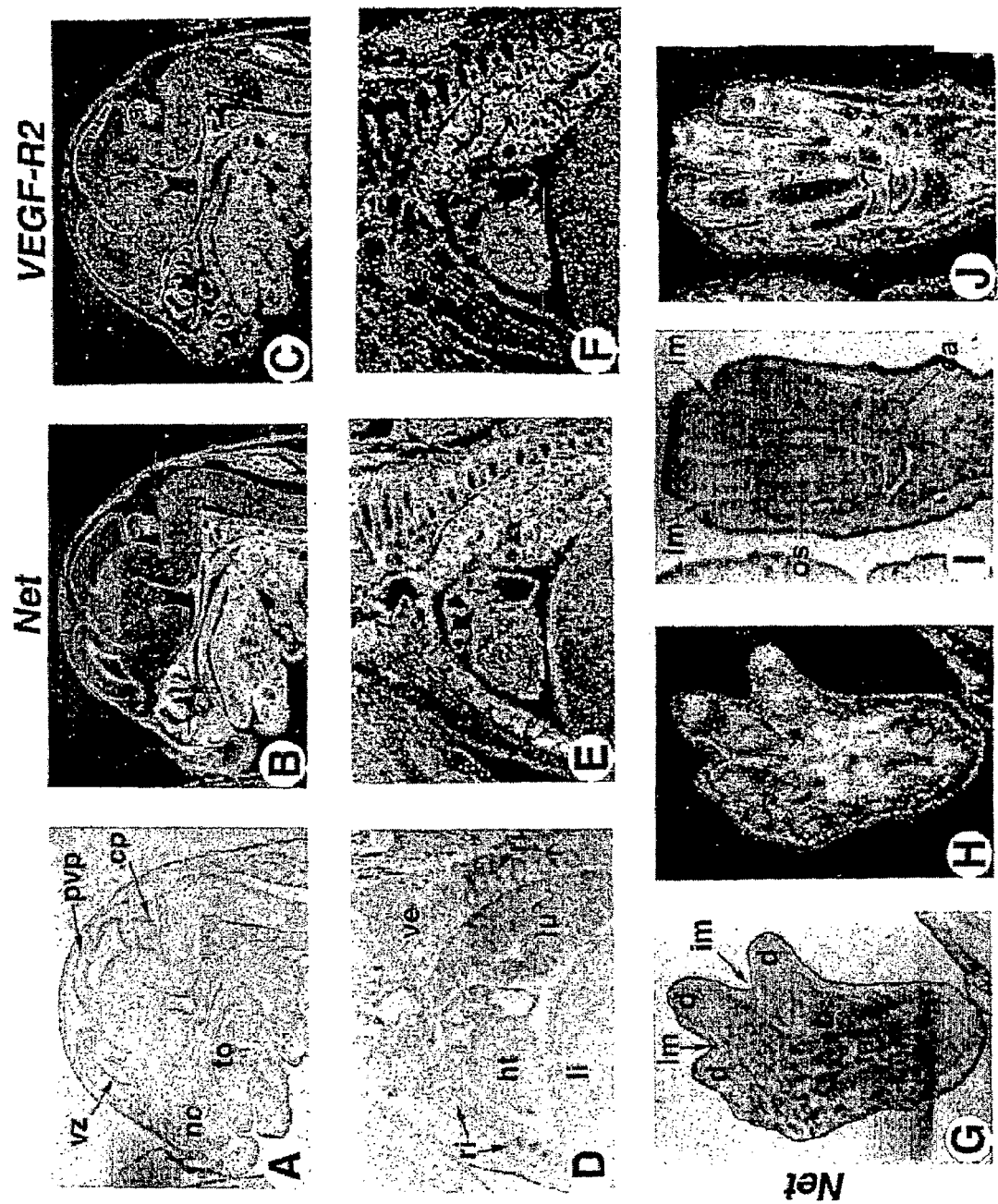

FIG. 21: Net and VEGF-R2 expression in adjacent sagittal sections at E16.5 (A-F), and Net expression during limb cartilage differentiation (G-J) at E14.5 and E16.5 stages. (B) and (E) show Net expression in the head and thoracic region respectively, whereas (C) and (D) represent the VEGF-R2 pattern. Abbreviations: ca, carsus; cp, choroid plexus; d, digit; im, interdigital mesenchyme; ht, heart; li, liver; lu, lung; nc, nasal cartilage; os, ossifying center; pvp, perineural vascular plexus; ri, ribs; ta, tarsus; to, tongue; ventricular zone.

Figure 22:
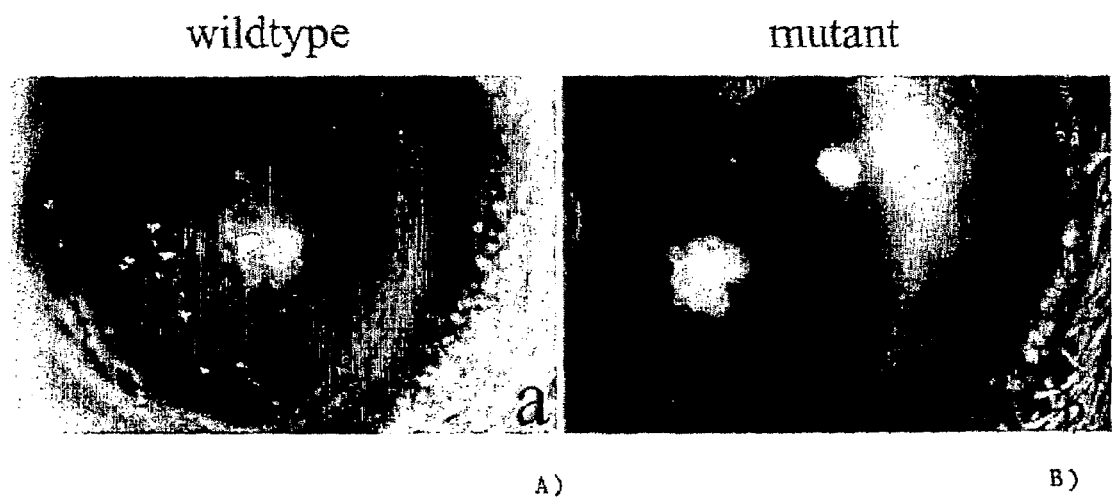

FIG. 22: Angiogenesis induced by rhFGF-2 in the cornea of mice. The technique was essentially as described in Kenyon et al. (*Invest. Ophthalmol. Vis. Sci.* 1996, 37: 1625-1632). Hydron pellets containing bFGF (90 ng) and sucrafate (4 5 ng) were implanted in the cornea of both Net wild-type and mutant mice. The eyes were examined by biomicroscopy 3-6 days after pellet implantation. (A) wildtype:(B) mutant.

Figure 23:
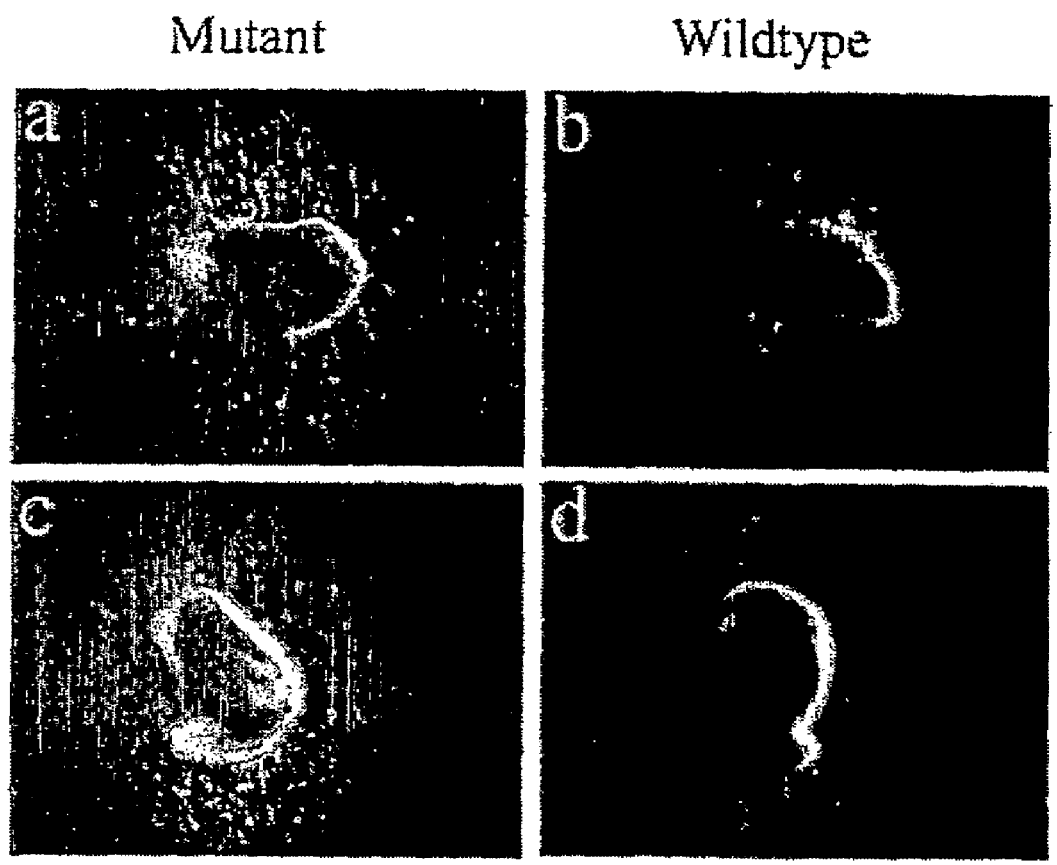

FIG. 23: Microvessel formation in the mouse aortic ring angiogenesis assay. The technique was essentially as described in Giovane et al (Genes Dev. 1994, 8, 1502-13). Twelve-well tissue culture grade plates were covered with 200 μl of Matrigel (Becton-Dickinson ) and allowed to gel for 30 min at 37° C. Thoracic aortas were excised front six to eight week-old Net wild-type and mutant mice. The aortic sections (1 mm long) were placed on their sides on top of this layer and immediately covered with 200 μl of Matrigel which was allowed to gel for 30 min. The rings were then incubated for 5 days with serum free media supplemented with a combination of growth factors optimised for endothelial cell growth (Clonetics, CA). On day 5, sprouts were examined with a microscope. Mutant (panel a and c); wildtype (panel b and d).

FIG. 24: Domains of Net polypeptide. FIG. 24*a* (human: SEQ ID No: 2), FIG. 24*b* (mice: SEQ ID No:4) A Box : (ets domain), lwqfllqlll (NES: SEQ ID No:18); B box (SRF interaction); NID (Net inhibitory domain); JEX (JNK interaction and export induced by phosphorylation); CID (CtBP interaction domain); D box (NLS and ERK1+p38 binding); C box (Phosphorylation induced transactivation).

DETAILED DESCRIPTION OF THE INVENTION

Because little is known about NET biological function, investigation was made to identify effect of NET deletion in transgenic mice in order to identify biological targets of its activity. The invention is based, in part, on the observation of the phenotype of such transgenic mice.

The invention accordingly relates to the use of the human cDNA encoding for the NET protein, homologs, splicing variants, single point or deletion mutants and the proteins encoded by these sequences for their use in screening for small molecules or natural products. Use of a 2-hybrid strain described in the examples, assessement of NET phosphorylation, modification of NET described activities, can be used in this process.

NET can also be used in gene therapy applications (both coding and antisense molecules can be of use) in order to modulate angiogenesis. The pathologies concerned by these gene therapies based on NET over-expression or down-regulation is discussed hereafter.

The pathologies related with angiogenic disorders include cancers and solid tumors for which antagonists of NET will act as antiangiogenic compounds (in a context in which Net is activated) and will lead to prevention, reduction or regression of tumor growth. Exemplary disorders for which the subject method or compounds can be used alone or as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilis' tumor, cervical cancer, testicular tumor, lung carcinoma, small cell lung carcinoma, bladder carcinoma, epithellal carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another preferred embodiment, the compound is a modulator of NET (either an agonist or an antagonist) and the compound can be used for prevention and/or treatment of pathologies related with angiogenic disorders in a context in which NET is not activated (or in a context in which cells are not transformed).

Such pathologies may involve insufficient vascularization and require increase of angiogenesis, these pathologies include but are not limited to cardiac or peripheral ischemia, defect of wound healing, vascular restenosis, decubitus or stasis ulcer, gastrointestinal ulcers, placental insufficiency, aseptic necrosis, impaired healing of bone fractures, pulmonary and systemic hypertension (vascular pruning), stroke, vascular dementia, alzheimer disease, CADASIL, thyroid pseudocyst, lymphoedema etc.

Such pathologies may also involve increased vascularization and require inhibition of angiogenesis, these pathologies include but are not limited to atherosclerosis, haemangioma, haemangioendothelioma, wart, hair growth, scar keloids, allergic oedema, dysfunctional uterine bleeding, follicular cysts, ovarian hyperstimulation, endometriosis, respiratory distress, ascites, peritoneal sclerosis (dialysis patients), adhesion formation (abdominal surgery), muscle and heart work overload, obesity, rheumatoid arthritis, synovitis, bone and cartilage destruction, osteomielitis, pannus growth, osteophyte formation, inflammation and infectious processes (hepatitis, pneumonia, glomerulonephritis), asthma, nasal polyps, transplantation of different organs (liver, kidney, . . . epithelia), retinopathy of prematurity, diabetic retinopathy, choroiral and other intraocular disorders, leuko malacia, thyroiditis, thyroid enlargement, pancreas transplantation, etc.

These and other aspects of the invention, particularly expression of NET protein, generation of anti-NET antibodies, screening assays for modulation of NET, screening assays for identifying antagonists or agonists of NET, and delivery of NET encoding vectors, in particular for gene therapy applications, are discussed in detail in the following sections. Section headers are provided merely for the reader's convenience, and are not to be deemed limiting in any respect.

Definitions

The present invention contemplates the use of a gene encoding a NET polypeptide, including a fall length, or naturally occurring form of NET, and any fragments thereof from any animal, particularly mammalian or avian, and more particularly human, source. As used herein, the term "gene" refers to an assembly of nucleotides that encode a polypeptide, and includes cDNA and genomic DNA nucleic acids. As used herein, "NET" refers to NET polypeptide, and "net" refers to a gene encoding NET polypeptide. NET protein is also known as Elk-3, Sap-2 and ERP. The nucleic acid sequence of human net gene is provided in SEQ ID No1, the corresponding polypeptide is given in SEQ ID No2. The nucleic acid sequence of murine net gene is provided in SEQ ID No3, the corresponding polypeptide is given in SEQ ID No4.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "cloning vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i. e., capable of replication under its own control. Cloning vectors may be capable of replication in one cell type, and expression in another ("shuttle vector").

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmaids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 550, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

As used herein, the term "oligonucleotide" refers to a nucleic acid, generally of at least 18 nucleotides, that is hybridizable to a genomic DNA molecule, a cDNA molecule, or an mRNA molecule encoding NET. Oligonucleotides can be labeled, e.g., with $^{32}$P-nucleotides or nucleotides to which a label, such as biotin, has been covalently conjugated (see the discussion, supra, with respect to labeling NET polypeptides). In one embodiment, a labeled oligonucleotide can be used as a probe to detect the presence of a nucleic acid encoding NET. In another embodiment, oligonucleotides (one or both of which may be labeled) can be used as PCR primers, either for cloning full length or a fragment of NET, or to detect the presence of nucleic acids encoding NET. In a further embodiment, an oligonucleotide of the invention can form a triple helix with a NET DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

A "Net antisense" a RNA or DNA molecule that is complementary to at least a portion of NET mRNA molecule. Such antisense polynucleotide can be employed to inhibit transcription and/or translation of Net polypeptide mRNA and thereby effects a reduction in the amount of Net polypeptide in the cell. A sequence coding for the Net antisense can be introduced on a vector and expressed in the cell. Alternatively, the Net antisense is a ssDNA or ssRNA, methylphosphonate backbone nucleic acid, phosphorothioate backbone nucleic acid, polyamide nucleic acid and the like antisense structures known in the art.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program, The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The present invention also contemplates the use of mammalian genes encoding NET, whether genomic DNA or cDNA, can be isolated from any source, particularly from a human cDNA or genomic library. Methods for obtaining net gene are well known in the art, as described above (see, e.g., Sambrook et al., 1989, supra).

Accordingly, any animal cell potentially can serve as the nucleic acid source for the molecular cloning of a net gene. The DNA may be obtained by standard procedures known in the art from cloned DNA (e.g., a DNA "library"), and preferably is obtained from a cDNA library prepared from tissues with high level expression of the protein (e.g., endothelial cells, fibroblasts, chondrocytes, thymus, spleen, cartilage)., by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The present invention also contemplates the use of genes (e.g., cDNAs) encoding allelic variants, splicing variants, analogs, and derivatives of NET, that have the same or homologous functional activity as NET, and homologs thereof from other species. The production and use of derivatives and analogs related to NET are within the scope of the present invention. In a specific embodiment, the derivative or analog is functionally active, i.e., capable of exhibiting one or more functional activities associated with a full-length, wild-type NET.

NET derivatives can be made by altering encoding nucleic acid sequences by substitutions, additions or deletions that provide for functionally equivalent molecules. Preferably, derivatives are made that have enhanced or increased functional activity relative to native NET.

Due to the degeneracy of nucleotide coding sequences, other DNA sequences which encode substantially the same amino acid sequence as a net gene, including an amino acid sequence that contains a single amino acid variant, may be used in the practice of the present invention. These include but are not limited to allelic genes, homologous genes from other species, and nucleotide sequences comprising all or portions of net genes which are altered by the substitution of different codons that encode the same amino acid residue within the sequence, thus producing a silent change. Likewise, the NET derivatives use in the invention include, but are not limited to, those containing, as a primary amino acid sequence, all or part of the amino acid sequence of a NET protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces b-turns in the protein's structure.

The genes encoding NET derivatives and analogs used in the invention can be produced by various methods known in the art. The manipulations which result in their production can occur at the gene or protein level. For example, the cloned net gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of NET, care should be taken to ensure that the modified gene remains within the same translational reading frame as the NET gene, uninterrupted by translational stop signals, in the gene region where the desired activity is encoded.

Additionally, the NET-encoding nucleic acid sequence can be mutated in vitro or in vivo, to create and/or destroy translation, initiation, and/or termination sequences, or to create variations in coding regions and/or modify splicing and/or form new restriction endonuclease sites or destroy preexisting ones, to facilitate further in vitro modification. In one embodiment and for purpose of the preparation of transgenic animal of the invention, such mutations inactivate Net function and preferentially destroy or modify translation and/or initiation sequences. In another embodiment and for the purpose of gene therapy, such mutations may enhance the functional activity of the mutated Net gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E.* coli, bacteriophages such as lambda derivatives, or plasmids such as pBR322 derivatives or pUC plasmid derivatives, e.g., pGEX vectors, pmal-c, pFLAG, etc. The insertion into a cloning vector can, for example; be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene or cDNA is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2 m plasmid.

Expression of NET Polypeptides

The nucleotide sequence coding for NET, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding NET is operationally associated with a promoter in an expression vector. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding NET and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant NET protein, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding NET is cultured in an appropriate cell culture medium under conditions that provide for expression of NET by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of NET protein may be controlled by any promoter/enhancer element known in the art, but these regulatory elements must be functional in the host selected for expression. Promoters which may be used to control NET gene expression include, but are not limited to, the SV40 early promoter region (Benoist and Chambon, 1981, Nature 290: 304-310), the promoter contained in the 3' long terminal repeat of Rous sarcoma virus (Yamamoto, et al., 1980, Cell 22:787-797), the herpes thyridine kinase promoter (Wagner et al., 1981, Proc. Natl. Acad. Sci. U.S.A. 78:1441-1445), the regulatory sequences of the metallothionein gene (Brinster et al., 1982, Nature 296:3942); prokaryotic expression vectors such as the b-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkiline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., 1988, Gene 67:31-40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI. and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive Rous Sarcoma Virus Long Terminal Repeat (RSV-LTR) promoter, hygromycin selectable marker; Invitrogen), pCEP4 (BamH1, SfiI, XhoI, NotI, NheI, HindIII, NheI, PvuII, and KpnI cloning site, constitutive human cytomegalovirus (hCMV) immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker; Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamH1 cloning site, RSV-LTR promoter, G418 selectable marker; Invitrogen), and pEBVHis RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/PSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and b-gal selection), pMJ601 (SalI, SmaI, AflI, NarI, BspMII, BamHI, ApaI, NheI, SacII, KpnI, and HindIII cloning site; TK- and b-gal selection), and pTKgptF1S (EcoRI, PstI, SalI, AccI, HindIII, SbaI, BamHI, and Hpa cloning site, TK or XPRT selection).

Yeast expression systems can also be used according to the invention to express NET. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterolinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, NET activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity; immunoaffinity, and sizing column chromatography), centrifugation, differential solubility, immunoprecipitation, or by any other standard technique for the purification of proteins.

Antibodies to NET

According to the invention, a NET polypeptide produced recombinantly or by chemical synthesis, and fragments or other derivatives or analogs thereof, including fusion proteins, may be used as an antigen or immunogen to generate antibodies that recognize the NET polypeptide. A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Such antibodies include but are not limited to polyclonal, monoclonal, chimeric, single chain, Fab fragments, and an Fab expression library. The anti-NET antibodies of the invention may be cross reactive, e.g., they may recognize NET from different species. Polyclonal antibodies have greater likelihood of cross reactivity. Alternatively, an antibody of the invention may be specific for a single form of NET, such as murine NET. Preferably, such an antibody is specific for human NET.

Various procedures known in the art may be used for the production of polyclonal antibodies to NET polypeptide or derivative or analog thereof. For the production of antibody, various host animals can be immunized by injection with the NET polypeptide, or a derivative (e.g., fragment or fusion protein) thereof, including but not limited to rabbits, mice, rats, sheep, goats, etc. In one embodiment, the NET polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the NET polypeptide, or fragment, analog, or derivative thereof, any technique that provides for the production of antibody molecules by continuous cell lines in culture may be used. These include but are not limited to the hybridoma technique originally developed by Kohler and Milstein [*Nature* 256:495-497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals [International Patent Publication No. WO 89/12690, published Dec. 28, 1989]. In fact, according to the invention, techniques developed for the production of "chimeric antibodies" [Morrison et al., *J. Bacteriol.* 159:870 (1984); Neuberger et al., *Nature* 312:604-608 (1984); Takeda et al., *Nature* 314:452-454 (1985)] by splicing the genes from a mouse antibody molecule specific for a NET polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain Fv (scFv) antibodies [U.S. Pat. Nos. 5,476,786 and 5,132,405 to Huston; U.S. Pat. No. 4,946,778] can be adapted to produce NET polypeptide-specific single chain antibodies. An additional embodiment of the invention utilizes the techniques described for the construction of Fab expression libraries [Huse et al., *Science* 246: 1275-1281 (1989)] to allow rapid and easy identification of monoclonal Fab fragments with the desired specificity for a NET polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a NET polypeptide, one may assay generated hybridomas for a product which binds to a NET polypeptide fragment containing such epitope. For selection of an antibody specific to a NET polypeptide from a particular species of animal, one can select on the basis of positive binding with NET polypeptide expressed by or isolated from cells of that species of animal.

The foregoing antibodies can be used in methods known in the art relating to the localization and activity of the NET polypeptide, e.g., for Western blotting, imaging NET polypeptide in situ, measuring levels thereof in appropriate physiological samples, etc. using any of the detection techniques mentioned above or known in the art.

In a specific embodiment, antibodies that agonize or antagonize the activity of NET polypeptide can be generated. Such antibodies can be tested using the assays described infra for identifying ligands. In particular, such antibodies can be scFv antibodies expressed intracellularly.

Screening Assays

Identification of role of Net in angiogenesis allows for designing and screening new anti- or pro-angiogenic compounds. Accordingly, in addition to rational design of agonists and antagonists based on the structure of NET polypeptide, the present invention contemplates an alternative method for identifying specific ligands of NET using various screening assays known in the art.

Any screening technique known in the art can be used to screen for NET agonists or antagonists or to screen for antagonists of NET/DNA binding.

The present invention contemplates screens for small molecule ligands or ligand analogs and mimics, as well as screens for natural ligands that bind to and agonize or antagonize activates NET in vivo. For example, natural products libraries can be screened using assays of the invention for molecules that agonize or antagonize NET activity.

Molecules or compounds that agonize or antagonize NET activity and/or that modulate NET/DNA interaction may provide new venue for preventing and/or treating pathologies which involve a deregulation of expression of genes controlled by Net and/or pathologies related with deregulation of angiogenesis.

With this regards, the invention also provides for a method for treating an individual having need to inhibit or activate NET activity or having need to regulate expression of genes under control of Net transcription factor comprising administering a therapeutically effective amount of molecules or compounds that agonize or antagonize NET activity and/or that modulate NET/DNA interaction. The invention provides for the use of such molecules or compounds for the preparation of a medicament.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249:386-390 (1990); Cwirla, et al., Proc. Natl. Acad. Sci., 87:6378-6382 (1990); Devlin et al., Science, 249:404-406 (1990)], very large libraries can be constructed ($10^6$-$10^8$ chemical entities). A second approach uses primarily chemical methods, of which the Geysen method [Geysen et al., Molecular Immunology 23:709-715 (1986); Geysen et al. J. Immunologic Method 102:259-274 (1987)] and the method of Fodor et al. [Science 251:767-773 (1991)] are examples. Furka et al. [14th International Congress of Biochemistry, Volume 5, Abstract FR:013 (1988); Furka, Int. J. Peptide Protein Res. 37:487-493 (1991)], Houghton [U.S. Pat. No. 4,631,211, issued Dec. 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad Sci. USA 90:10700-4 (1993); Ohlmeyer et al., Proc. Natl. Acad Sci. USA 90:10922-10926 (1993); Lam et al., International Patent Publication No. WO 92/00252; Kocis et al., International Patent Publication No. WO 9428028, each of which is incorporated herein by reference in its entirety], and the like can be used to screen for NET ligands according to the present invention.

The screening can be performed with recombinant cells that express NET, or alternatively, using purified protein, e.g., produced recombinantly, as described above. For example, the ability of labeled, soluble NET that includes the DNA-binding portion of NET or protein-binding portion of NET, can be used to screen libraries, as described in the foregoing references.

In one embodiment, NET may be directly labeled. In another embodiment, a labeled secondary reagent may be used to detect binding of a NET to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two color assays may be performed with two or more colored latex beads, or fluorophores that emit at different wavelengths. Labeled may be detected visually or by mechanical/optical means. Mechanical/optical means include fluorescence activated sorting, i.e., analogous to FACS, and micromanipulator removal means.

As exemplified herein, the level of the NET protein can be evaluated by metabolic labeling of the proteins. As the metabolic labeling occurs during in vitro incubation of the tissue biopsy in the presence of culture medium supplemented with [$^{35}$S]-methionine, the level of each of the markers detected may be affected by the in vitro conditions. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions). Thus, a sample or library of compounds can be directly analyzed after labeling of the proteins therein, e.g., by colorimetric staining using silver, gold, coomassie blue, or amido-schwartz, to mention a few techniques; isotopic labeling, e.g., with [$^{32}$P]-orthophosphate, [$^{125}$I], [$^{131}$I]; fluorescent or chemiluminescent tags; and immunological detection with labeled antibody or specific binding partner of a marker.

NET cDNA and derivatives can also be used in a two-hybrid system in yeast screening to identify ligands to NET, agonists or antagonists of NET/DNA binding and to identify proteins that are able to phosphorylate or to prevent Net phosphorylation.

Modulator of Net Transcription Factor Activity

Several compounds were identified as modulator of Net transcription factor by the applicants such as inhibitor of p38 signalling pathway SB203580: 4-[5-(4-fluorophenyl)4-4-(pyridinyl)-1H-imidazol-2-yl]phenyl methyl sulfoxide or inhibitors of ERK signalling pathway: PD98059 2-(2-amino-3-methoxyphenyl)-4H-chromen4-one and U0126: 1,4-di-amino-2,3-dicyano-1,4 bis[2-aminophenylthio]butadiene Pharmaceutical Compositions Any compounds or NET antisense, of the invention will preferably be introduced in vivo in a pharmaceutically acceptable vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Transgenic Animals

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possesses some or all of that information, then they, too, are transgenic animals.

The information may be foreign to the species of animal to which the recipient belongs, foreign only to the particular individual recipient, or genetic information already possessed by the recipient. In the last case, the introduced gene may be differently expressed compared to the native endogenous gene.

The genes may be obtained by isolating them from genomic sources, by preparation of cDNAs from isolated RNA templates, by directed synthesis, or by some combination thereof.

To be expressed, a gene should be operably linked to a regulatory region. Regulatory regions, such as promoters, may be used to increase, decrease, regulate or designate to certain tissues or to certain stages of development the expression of a gene. The promoter need not be a naturally occurring promoter. The "transgenic non-human animals" of the invention are produced by introducing "transgenes" into the germline of the non-human animal. The methods enabling the introduction of DNA into cells are generally available and well-known in the art. Different methods of introducing transgenes could be used. Generally, the zygote is the best target for microinjection. In the mouse, the male pronucleus reaches the size of approximately 20 µm in diameter, which allows reproducible injection of 1-2 pL of DNA solution. The use of zygotes as a target for gene transfer has a major advantage. In most cases, the injected DNA will be incorporated into the host gene before the first cleavage (Brinster, et al., (1985) *Proc. Natl. Acad Sci.* USA 82, 4438-4442). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is a preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection (Jaenich, R. (1976) *Proc. Natl. Acad. Sci.* USA 73, 1260-1264). Efficient infection of the blastomeres is obtained by enzymatic treatment to remove the zona pellucida (Hogan et al., (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner et al., (1985) *Proc. Natl. Acad. Sci.* USA 82, 6927-6931; Van der Putten et al., (1985) *Proc. Natl. Acad. Sci.* USA 82 6148-6152). Transfection is easily and efficiently obtained by culturing the blastomeres on a monolayer of virus-producing cells (Van der Putten, supra; Stewart et al., (1987) EMBO J. 6:383-388). Alternatively, infection can be performed at a later stage. Virus or virus-producing cells can be injected into the blastocele (Jahner et al., (1982) *Nature* 298:623-628). Most of the founder animals will be mosaic for the transgene since incorporation occurs only in a subset of the cells which formed the transgenic non-human animal. Furthermore, the found animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) supra).

A third type of target cell for transgene introduction is the embryonal stem cell (ES). ES cells are obtained from pre-implantation embryos cultured in vitro (Evans, M. J., et al., (1981) *Nature* 292 154-156; Bradley, A., et al. (1984) *Nature* 309,255-258; Gossler, et al., (1986) *Proc. Natl. Acad. Sci.* USA 83, 9065-9060; and Robertson, et al., (1986) *Nature* 322, 445-448). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R. (1988) *Science* 240, 1468-1474).

The methods for evaluating the presence of the introduced DNA as well as its expression are readily available and well-known in the art. Such methods include, but are not limited to DNA (Southern) hybridization to detect the exogenous DNA, polymerase chain reaction (PCR), polyacrylamide gel electrophoresis (PAGE) and Western blots to detect DNA, RNA and protein. The methods include immunological and histochemical techniques to detect MDM2.

As used herein, a "transgene" is a DNA sequence introduced into the germline of a non-human animal by way of human intervention such as by way of the Examples described below.

Gene Therapy and Transgenic Vectors

As discussed above, a "vector" is any means for the transfer of a nucleic acid according to the invention into a host cell. Preferred vectors are viral vectors, such as retroviruses, herpes viruses, adenoviruses, and adeno-associated viruses. Thus, a gene or a cDNA encoding NET or NET polypeptide domain fragment thereof, or NET ScFv or NET mutant dominant or a NET antisense is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Expression vectors of the invention can be used, as pointed out above, both to transfect cells for screening or biological testing of modulators of NET activity, or for delivery of a net gene or net antisense gene in vivo or ex vivo for gene therapy, e.g., to increase or decrease the level of NET activity. A vector that expresses an anti-NET scFv can also be introduced using the techniques discussed below.

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillornavirus, Epstein Barr virus (EBV), adenovirus, adeno-associated virus (AAV), vaccinia virus, lentivirus, and the like. Defective viruses, which entirely or almost entirely lack viral genes, are preferred. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., *Molec. Cell. Neurosci.* 2:320-330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626-630 (1992); see also La Salle et al., *Science* 259:988-990 (1993)]; and a defective adeno-associated virus vector [Samulski et al., *J Virol.* 61:3096-3101 (1987); Samulski et al., *J. Virol.* 63:3822-3828 (1989); Lebkowski et al., *Mol. Cell. Biol.* 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

The invention contemplates delivery of a vector that will express a therapeutically effective amount of NET antisense or NET ScFv or NET dominant mutant for gene therapy applications. Examples of NET dominant mutant are such as C12 or GAL-N6 are provided in Maira et al. (EMBO J. (1996) 15:5849-65). The phrase "therapeutically effective amount" is used herein to mean an amount sufficient to reduce by at least about 15 percent, preferably by at least 50 percent, more preferably by at least 90 percent NET activity, and most preferably prevent, a clinically significant inhibition of NET activity or deregulation of expression of genes controlled by NET. Alternatively, a therapeutically effective amount is sufficient to cause an improvement in a clinically significant condition in the host.

Alternatively, the invention contemplates delivery of a vector that will express a therapeutically effective amount of NET for gene therapy applications. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Any vector, viral or non-viral, of the invention will preferably be introduced in vivo in a pharmaceutically acceptable vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Adenovirus Vectors

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and W095/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is carried out following cotransfection of the adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art. The invention also relates, therefore, to a defective recombinant adenovirus whose genome encompasses a sequence encoding a gene or a cDNA encoding NET or NET polypeptide domain fragment thereof, or NET ScFv or NET mutant dominant.

Adeno-Associated Virus Vectors

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a gene or a cDNA encoding NET or NET polypeptide domain fragment thereof, or NET ScFv or NET mutant dominant flanked by the AAV ITRs. The invention also relates to a plasmid encompassing a sequence encoding NET or NET polypeptide domain fragment thereof, or NET ScFv or NET mutant dominant flanked by two ITRs from an AAV. Such a plasmid can be used as it is for transferring the nucleic acid sequence, with the plasmid, where appropriate, being incorporated into a liposomal vector (pseudo-virus).

Retrovirus Vectors

In another embodiment the net gene or cDNA encoding NET or NET polypeptide domain fragment thereof, or NET ScFv or NET mutant dominant can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsulation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infection particles or to undergo a single round of transfection. In the former case, the virus is modified to retain all of its genes except for those responsible for oncogenic transformation properties, and to express a gene or a cDNA encoding NET or NET polypeptide domain fragment thereof, or NET ScFv or NET mutant dominant. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional viruses.

Targeted gene delivery is described in International Patent Publication WO 95/28494, published October 1995.

Non-viral Vectors

Alternatively, the vector comprising a gene or a cDNA encoding NET or NET polypeptide domain fragment thereof, or NET ScFv or NET mutant dominant NET can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., Proc. Natl. Acad. Sci. U.S.A. 84:7413-7417 (1987); see Mackey, et al., Proc. Natl. Acad. Sci. U.S.A. 85:8027-8031 (1988); Ulmer et al., Science 259: 1745-1748 (1993)]. The use of cationic lipids may promote encapsulation of negatively charged nucleic acids, and also promote fusion with negatively charged cell membranes [Felgner and Ringold, Science 337:387-388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/2193 1), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963-967 (1992); Wu and Wu, J. Biol. Chem. 263:14621-14624 (1988); Hartmut et al., Canadian Patent Application No. 2,012,311, filed Mar. 15, 1990; Williams et al., Proc. Natl. Acad Sci. USA 88:2726-2730 (1991)]. Receptor-mediated DNA delivery approaches can also be sued [Curiel et al., Hum. Gene Ther. 3:147-154 (1992); Wu and Wu, J. Biol. Chem. 262:4429-4432 (1987)].

The invention also relates, therefore, to a plasmid which comprises a sequence encoding a gene or a cDNA encoding NET or NET polypeptide domain fragment thereof, or NET ScFv or NET mutant dominant The present invention may be better understood by reference to the following non-limiting Examples, which are provided as exemplary of the invention.

Material and Method:

Plasmids and Cell Lines pCEFL, pCEFL-GPCR, p601D-antisense NET and p601D (empty vector) have been described in Giovane et al. (Genes Dev. 1994, 8, 1502-13).

Gal4-N5 has been described in Maira et al. (EMBO J. (1996) 15:5849-65)

pRAS V12, Δ Ras, have been described in Giovane et al. (Genomics (1995) 29:769-72.)

Microtubules Formation a. NIH3T3 cells (C11) were transfected by the calcium phosphate technique with pCEFL-KSHVGPCR (mouse EF12 promoter) and the AntiNet expression vector or the corresponding empty vector (p601D: Beddinton et al.1989, Development 106:37-46). 16 hours after applying the precipitate, the cells were washed twice with DMEM, incubated in DMEM with 0,05% FCS for 48 hours. The medium was collected and either tested immediately or stored at −80° C.

b. HUVEC cells (passage 4-6) were grown in DMEM/F12K containing 10% FCS, Heparine (50 ng/mnl), ECGF (Endothelial Cell Growth Factor, Sigma, 50 ng/ml) and Glutamine (2 mM).

c. The wells of 24-multiwell plates were coated with 120 ml/well of Growth Factor Reduced MATRIGEL Matrix (Collaborative Biomedical Products) at 4° C. and incubated for 30 min at 37° C.

d. Trypsinised HUVEC cells were resuspended in DMEM/F12K containing 0.5-1.0% FCS, Heparine (50 ng/ml) and Glutamine(2 mM) and then seeded in the Matrix coated wells (10,000 cells per well). Once the cells were attached (around 4-6 hours), the conditioned media from step "a" were added (1:1 volume:volume). The plates were observed after 16-24 hours.

e. Anti-VEGF antibody inhibition and recombinant VEGF stimulation of angiogenic activity in vitro. Conditioned media from step "a" were incubated with 0.2 mg/ml of anti-mouse-VEGF polyclonal antibody (R&D) or with 50 ng/ml recombinant human VEGF (R&D) for 1 hour at 37° C., and then added to the Matrix coated and HUVEC seeded wells as in step "d".

The plates were observed after 16-24 hours.

Genotyping of ES Cell, Embryos and Mice

Genomic DNA from ES cells or tail biopsies was isolated and resuspended in 100 μl 10 mM Tris-HCl pH 8.0, 1 mM EDTA. To determine the genotype, 15 μl of DNA were digested with XbaI, and analysed by Southern blotting using a 3.8 kb probe isolated from the 3' region outside of the targeting construct. For routine analysis, mice are genotyped by PCR using the allele-specific primers: UC54 (SEQ ID No5), UC56 (SEQ ID No6) and UC57 (SEQ ID No7). The PCR conditions were 1 cycle at 94° C. for 2 min followed by 30 cycles at 94° C. for 30 sec, 64° C. for 30 sec and 72° C. for 45 sec, and 1 cycle at 72° C. for 5 min. 0.5 μl DNA was used in a 25 μl reaction containing 200 ng of each primer plus the PCR reagents according to manufacturer's instructions (Sigma). The size of the products are 1550 bp from the wild-type and 1300 bp from the targeted allele.

RT-PCR Protocole

RNA was extracted from mouse tissues with Trizol (Gibco/BRL) as specified by the manufacturer. 1 μg of total RNA was used for the reverse transcription with different exon-specific primers. The conditions for the amplification reaction are described by Giovane et al. (Genomics, 1995, 29: 769-72). The pair of primers used was as follows:

EX1 (SEQ ID N°8)/EX2a (SEQ ID N°9):
CTAGAAATCTCCCCAAGAAGACTC/GTTGTCGTCATAGTATCTCAGCGC

EX2b (SEQ ID N°10)/EX3a (SEQ ID N°11):
TGCTGGACATCGAACGATGGCGAG/ACTTGTACACAAACTTCTGCCCGA

EX3b (SEQ ID N°12)/EX4 (SEQ ID N°13):
CTGGAGCCCCTGAATCTGTCATCG/TCGAGGCCAGAAACAGTCCACTTG

EX1 (SEQ ID N°8)/EX3a (SEQ ID N°11)
CTAGAAATCTCCCCAAGAAGACTC/ACTTGTACACAAACTTCTGCCCGA

The PCR products were analysed by electrophoresis on 5% polyacrylamide gels, staining with ethydium bromide, and visualisation under U.V.

Western Blots

Tissues were extracted with RIPA buffer (150 mM NaCl, 1% NP-40, 0.5% deoxycholic acid, 0.1% SDS, 50 mM Tris-HCl pH 8.0, 2 µg/ml aprotinin, 2 µg/ml leupeptin, and 100 µg/ml phenylmethylsulphonylfluoride) using an Ultraturax homogenizer. Protein (200-300 µg) were electrophoresed on 10% SDS PAGE, transferred to nitro-cellulose membranes and detected with the purified 375 antibody and the enhanced chemiluminescence detection kit (Amersham).

EXAMPLES

Example 1

Angiogenesis Induced by KSHV/HHV8 ORF 74 is Mediated by Net.

*Kaposi sarcoma* virus (KSHV/HHV8) stimulates angiogenesis (Boshoff, Nature, 391, 24-25 (1998). Its ORF 74 codes for a G-protein coupled receptor (GPCR) that is transforming and induces an angiogenic phenotype through a pathway involving the ERK and p38 kinase signalling cascades and VEGFa. GPCR expression in NIH3T3 induces the secretion of angiogenic factors into the medium, principally VEGFa (Bais et al., 1998). The conditioned medium induced microtube formation by human umbilical vein endothelial cells (HUVEC) growing in Matrigel (FIG. 1a) and antibodies against VEGFa neutralise this activity (FIG. 1b) [see (Bais et al., Nature, 391, 86-89 (1998)].

In order to determine whether Net is involved in angiogenesis induced by KSVH/HHV8 ORF74, microtubule formation by conditioned medium from GPCR expressing cells was tested when Net is down-regulated by either anti-sense net RNA or a trans-dominant Net mutant (Gal.Net 219-409=Gal4.N5).

The technique is essentially as described in (Bais et al., 1998). NIH3T3 cells were maintained in Dulbecco's modified Eagle's medium (DMEM) containing 10% fetal calf serum (FCS) and transfected by the BBS calcium phosphate method in 6-well plates with pCEFL-GPCR alone; pCEFLG-PCR with p601D-antisense-Net or p601D-transdominant-Net. 16 hours later, cells are washed and maintained in fresh media for 24 hours. Before incubation with HUVEC cells, some of the conditioned media were incubated with either: (b) 0.2 µg/ml of anti-mouse-VEGF polyclonal antibody (total goat IgG; R&D SYSTEMS) or with (d and f) 10 ng/ml of recombinant human VEGF (R&D) for 1 hour at 21° C. The wells of a 24-multiwell plate were coated with 150 µl per well of MATRIGEL (Becton Dickinson Labware) and incubated for 30 min at 37° C. HUVEC cells in medium with 10% calf serum (105 per well) were added and conditioned media was added once the cells had attached. The plates were observed after 24 hours (phase contrast, original magnification, ×40).

Figure 1:
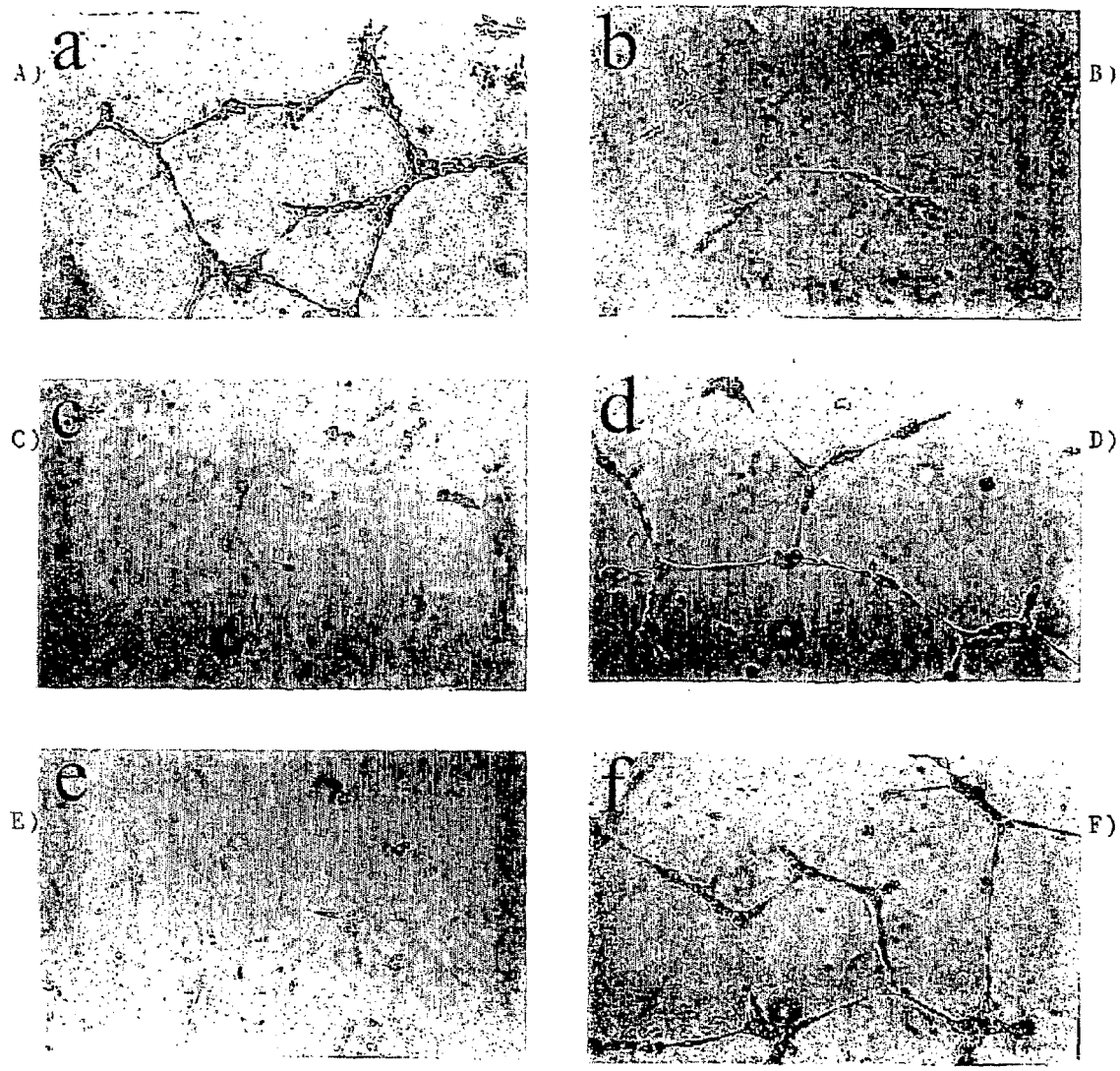
FIG. 1: Microtubule formation by HUVEC cells on Matrigel induced by conditioned media from differentially transfected NIH3T3 cells. NIH3T3 cells were transfected by pCEFL-GPCR alone (FIG. 1a); pCEFL-GPCR with p601D-antisense-Net (FIG. 1c) or p601D-transdominant-Net (FIG. e). Before incubation with HUVEC cells, some of the conditioned media were incubated with either: (b) 0.2 μg/ml of anti-mouse-VEGF polyclonal antibody (total goat IgG; R&D SYSTEMS) or with (d and f) 10 ng/ml of recombinant human VEGF-A (R&D). The plates were observed after 24 hours (phase contrast, original magnification, ×40).

Microtubule formation by conditioned medium from GPCR expressing cells was inhibited when Net is down-regulated by either anti-sense net RNA (FIG. 1c) or a trans-dominant Net mutant (Gal.Net 219-409; FIG. 1e).

VEGFa production is involved in this inhibition since adding VEGFa to the conditioned medium restored microtubule inducing activity (compare FIGS. 1d and c, and 1f and 1e).

Conditioned medium from GPCR expressing NIH3T3 stimulates proliferation of HUVEC cells growing on culture plates [see (Bais et al., 1998)]. In order to determine the effect of down-regulation of Net on GPCR induced proliferation of HUVEC, the HUVEC cell proliferation was tested when Net is down-regulated by either anti-sense net RNA or a trans-dominant Net mutant (Gal.Net 219-409, TD).

NIH3T3 cells were transfected as described above with the control vector for GPCR (pCEFL); the vector for GPCR with the control vector for antisense-Net (p601D); the vectors for GPCR and antisense-Net or transdominant (TD)-Net. HUVEC cells ($10^5$) in medium with 10% calf serum were added per well (6-well clusters, Costar 3516), and conditioned media were added once cells were attached. 48 hours later, the cells were trypsinized, resuspended in 1 ml medium and living cells were counted after Trypan blue staining.

Figure 2:
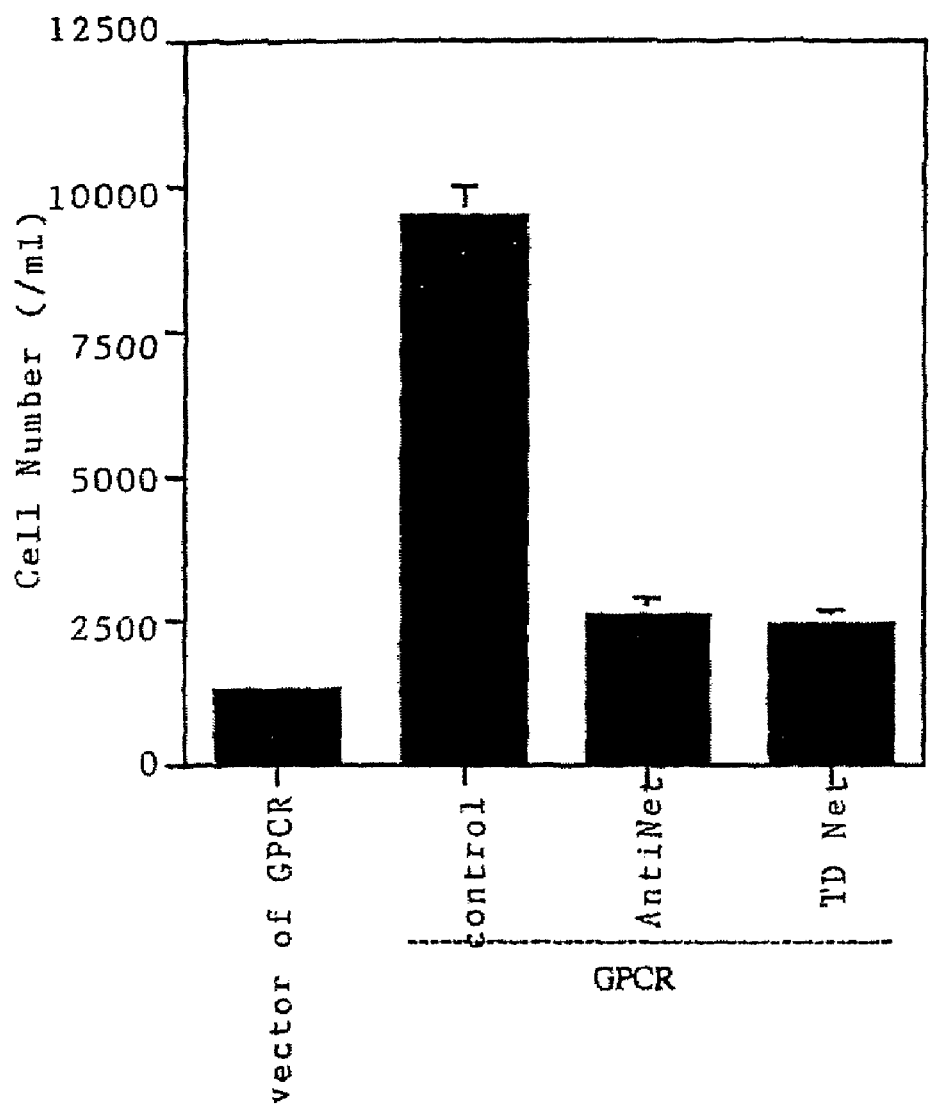
FIG. 2: HUVEC cell proliferation in conditioned media. NIH3T3 cells were transfected with the control vector for GPCR (pCEFL); the vector for GPCR with the control vector for antisense-Net p601D); the vectors for GPCR and antisense-Net or transdominant (TD)-Net.

The results demonstrate that down-regulation of Net with either anti-sense net RNA or a trans-dominant (TD) protein reduced GPCR induced proliferation of HUVEC (FIG. 2). The control showed that conditioned medium from GPCR expressing NIH3T3 stimulates proliferation of HUVEC cells growing on culture plates [see FIG. 2, compare GPCR and the control vector].

In the following examples, the mechanism of GPCR induced angiogenesis through Net was found to involve GPCP activation of ERK and p38 MAP kinase signalling cascades, phosphorylation of endogenous Net, activation of transcription of the VEGFa promoter, and secretion of the VEGFa peptide.

Example 2

The Mechanism of GPCR Induced Angiogenesis through Net Involve Phosphorylation of Endogenous Net Phosphorylation of endogenous Net was followed with a phospho-specific antibody that recognises phospho-serine 365, which is important for phosphorylation induced activation of Net by ERK and p38 signalling cascades.

NIH3T3 cells were transfected as described above with the control vector for GPCR (pCEFL) or the vector for GPCR (pCEFL-GPCR). 14 hours later, cells were washed and left in the growth medium for 2.5 hours. The cells were then treated with SB 203580 (10 µM) (Alexis Corp.) or U0126 (10 µM) (Promega) for 30 min. After 6 hours, extracts were analysed by SDS-PAGE and Western-blotting with antibodies against phospho-serine 365 Net [Antibody 2F3, Giovane et al. (Genomics (1995) 29:769-72)] or activated ERK (Promega).

Figure 3:
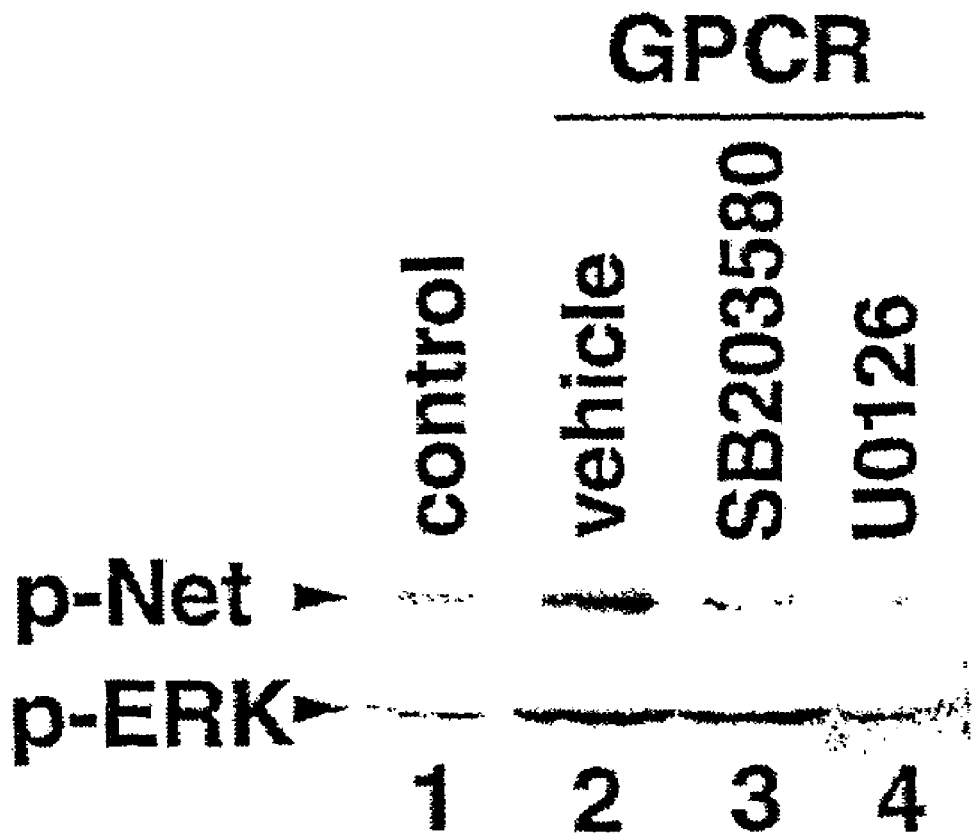
FIG. 3: Phosphorylation of endogenous Net. NIH3T3 cells were transfected as described above with the control vector for GPCR (pCEFL) (line 1) or the vector for GPCR (Line 2). 14 hours later, cells were washed and left in the growth medium for 2.5 hours. The cells were then treated with SB 203580 (10 μM) (Alexis Corp.) or U0126 (10 μM) (Promega) for 30 min. After 6 hours, extracts were analysed by SDS-PAGE and Western-blotting with antibodies against phospho-serine 365 Net (antibody 2F3, Ducret et al. (Oncogene, in press) or activated ERK (Promega).

Results are presented in FIG. 3. GPCR induced phosphorylation of Net (lanes 1,2), and the induction was dependent on both the p38 and ERK pathways, as show by the inhibitors SB 203580 and U 0126, respectively (lanes 3, 4; note that SB 203580 did not inhibit ERK activation under the conditions used).

Similar conclusions were reached by following phosphorylation of transfected Net, and in a trans-activation assay using Gal4-Net (219-409) (data not shown). These data show that GPCR. induces phosphorylation and activation of Net through both the ERK and p38 pathways. It follows that inhibitors of p38 pathway or ERK pathway should prevent NET phosphorylation and thus prevent angiogenesis induced by GPCR.

Example 3

The Mechanism of GPCR Induced Angiogenesis through Net Involves Activation of Transcription of the VEGFa Promoter The role of Net upon VEGF promoter activation by GPCR was tested when Net is down-regulated by anti-sense net RNA.

NIH3T3 cells were transfected as described above by control vector of GPCR (pCEFL)+control vector of antisense-Net (p601D); pCEFL+antiNet; GPCR+p601D; GPCR+Anti-Net with the reporters: mdm2-Luc; p21-Luc; VEGF-Luc and pCMV-LacZ. The cells were harvested, lysed and luciferase assays were performed as by standard techniques.

Figure 4:
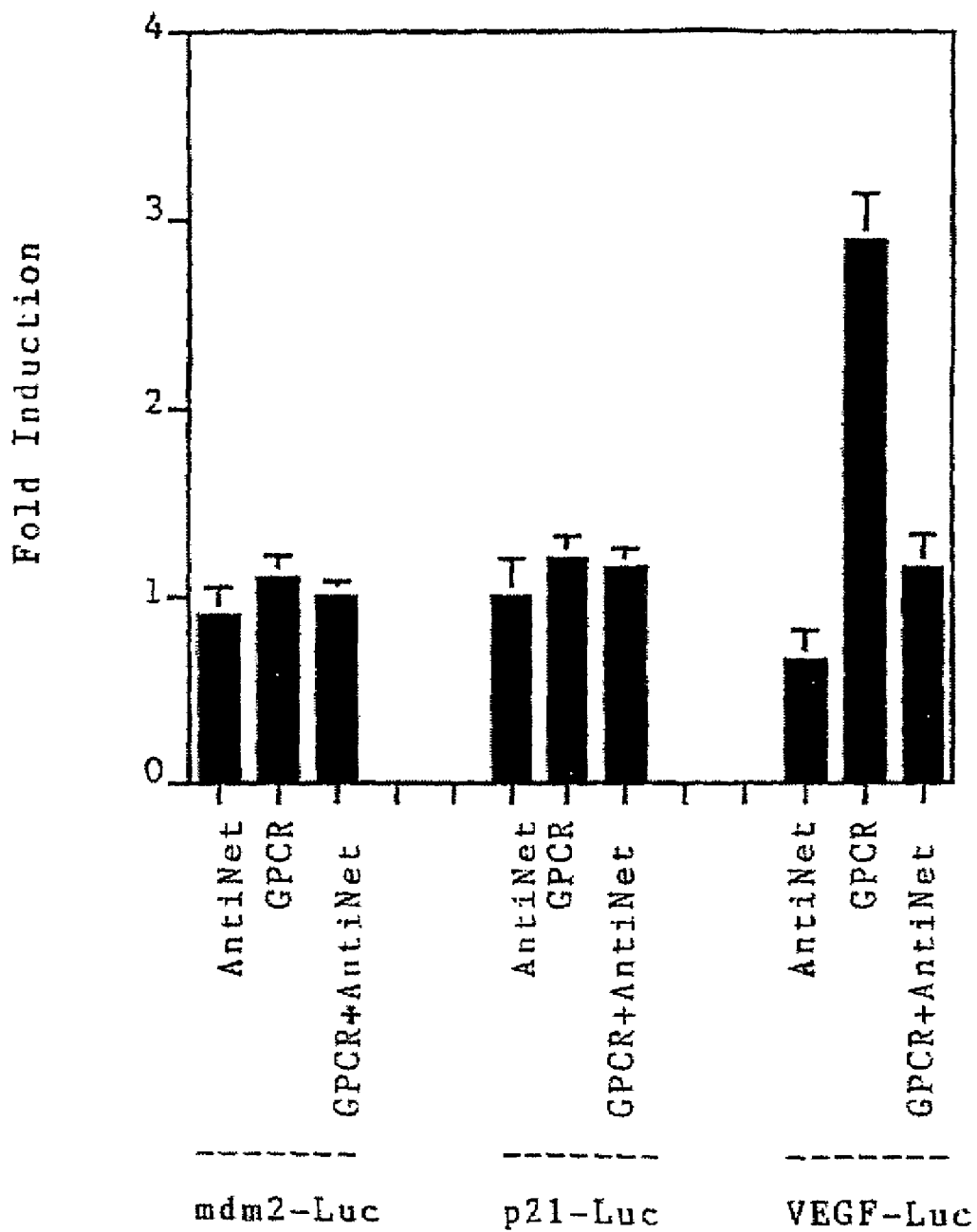
FIG. 4: VEGF promoter activation by GPCR requires Net. NIH3T3 cells were transfected as described above by control vector of GPCR (pCEFL)+control vector of antisense-Net (p601D); pCEFL+antiNet; GPCR+p601D; GPCR+AntiNet with the reporters: mdm2-Luc; p21-Luc; VEGF-Luc and pCMV-LacZ. The cells were harvested, lysed and luciferase assays were performed as by standard techniques.

GPCR was found to activate the VEGFa promoter in trans-activation assays (se FIG. 4). Down-regulation of Net with anti-sense inhibited GPCR activation of the VEGFa promoter. Down-regulation appears to be specific, in that antisense net did not affect the activities of the mdm2 and p21WAF1 promoters in the presence of GPCR.

Example 4

The Mechanism of GPCR Induced Angiogenesis through Net Involves Secretion of the VEGEa Peptide In order to test whether GPCR expression in fibroblasts induced secretion of the VEGFa peptide, equal amounts of NIH3T3 cells were transfected as described above by pCEFL (vector of GPCR) ; GPCR+p601D (control vector for Anti-Net) ; GPCR+AntiNet; Δ Ras; Ras-V12+p601D; Ras-V12+AntiNet; p601D; AntiNet with puromycin expression vector. 2 nM of puromycin was added after the wash. 48 hours later, conditioned media were harvested and cells were trypsinized, resuspended in 1 ml medium and living cells were counted following Trypan blue staining. VEGF peptide levels were measured by ELISA (Mouse-VEGF Quantikine kit, R&D) and the results were corrected for cell numbers.

Figure 5:
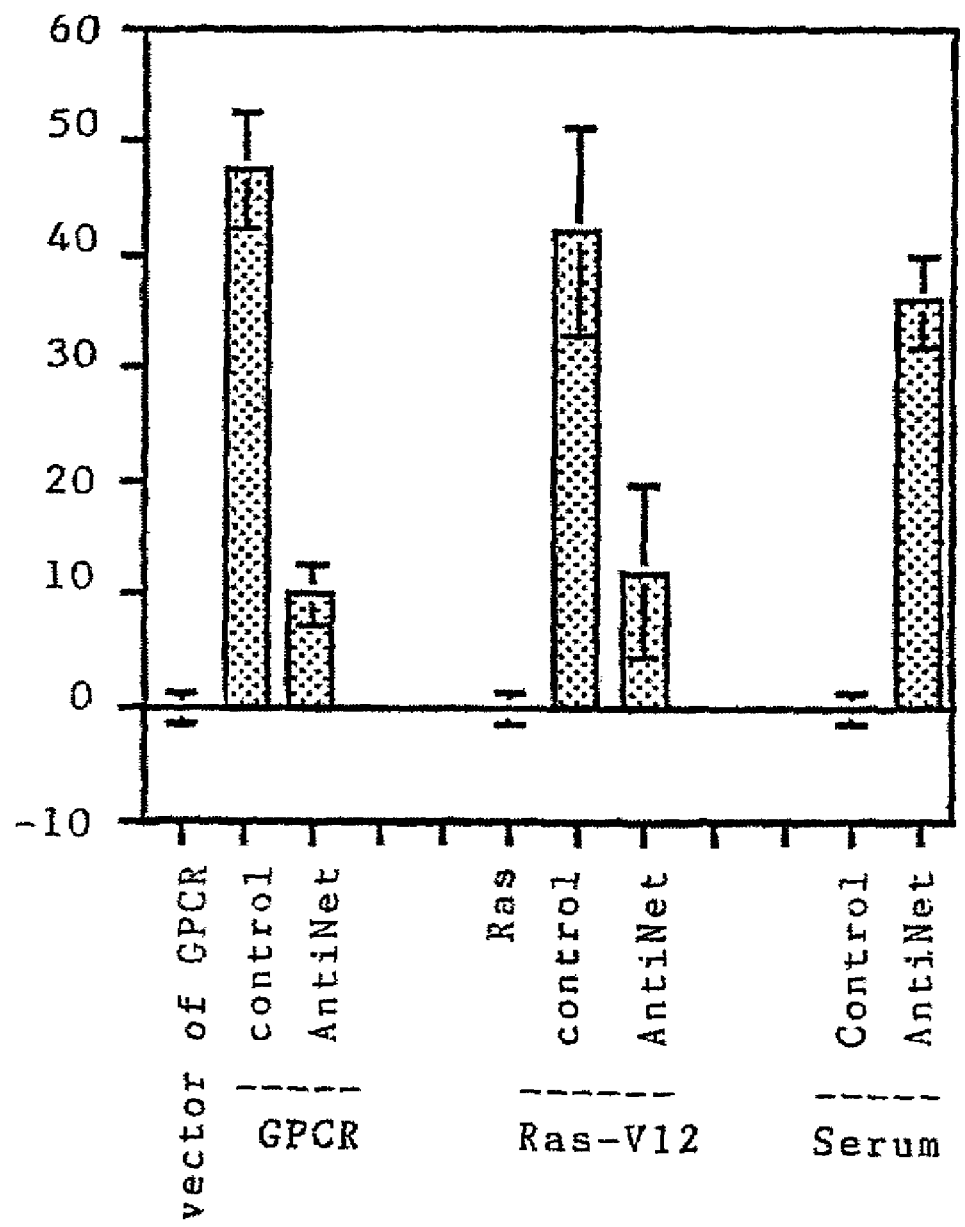
FIG. 5: VEGF peptide levels in conditioned media from transfected NIH3T3 cells. Equal amounts of NIH3T3 cells were transfected as described before by pCEFL (vector of GPCR); GPCR+p601D (vector of antiNet) ;GPCR+AntiNet; Δ Ras (inactive control for Ras V12); Ras-V12+p601D; Ras- V12+AntiNet; p601D; AntiNet with puromycin expression vector (pSG5 Puro). 2 nM of puromycin was added after the wash. 48 hours later, conditioned media were harvested and cells were trypsinized, resuspended in 1 ml medium and living cells were counted following Trypan blue staining. VEGF peptide levels were measured by ELISA (Mouse-VEGF Quantikine kit, R&D) and the results were corrected for cell numbers.

GPCR expression in fibroblasts induced secretion of the VEGFa peptide into the medium as shown in FIG. 5 by comparison of GPCR vector with the control vector. Anti-sense net inhibited VEGFa peptide secretion into the medium.

The Ras oncogene stimulates both VEGFa expression (Arbiser et al., PNAS USA, 94, 861-866 (1997)) and Net activity (Giovane et al., Gene Dev, 8, 1502-1513, (1994)).

The results show that VEGFa peptide secretion induced by Ras-V12 was inhibited by net-antisense.

Under non-induced conditions Net is a repressor (Giovane et al., 1994). Net antisense in the absence of activators increased VEGFa peptide levels, showing that under basal conditions Net is a repressor of VEGFa production.

This example demonstrates that in the absence of Net activator (Ras oncogene for example), the inhibition of Net expression or the inhibition of Net activity can promote angiogenesis through augmentation of VEGFa peptide secretion.

This example also demonstrates that when Net is activated (by Ras oncogene for example), the inhibition of Net expression or the inhibition of Net activity can inhibit or reduce angiogenesis through decrease of VEGFa peptide secretion.

This example also demonstrates that when Net is activated through phosphorylation via the ERK and/or the p38 pathway (by GPCR for example), the inhibition of Net expression or the inhibition of Net activity in such context can inhibit or reduce angiogenesis through decrease of VEGFa peptide secretion.

Inhibition of Net expression can be obtained with antisense Net, such as for example the complete cDNA in reverse orientation in Eco RI site of p601D (Giovane et al. Gene Dev. 1994, 8 1502-13), scFV, ds RNA. Inhibition of Net activity can be obtained by Net dominant Gal-Net such as Gal.N5 or C12 or by inhibitors of phosphorylation or by inhibitors of Net nuclear translocation.

Example 5

Down Regulation of NET Reduces VEGFa Secretion

In order to study the role of down regulation of NET on VEGFa secretion, stable clones of NIH3T3 cells expressing GPCR with or without anti-sense net were prepared.

Figure 6:
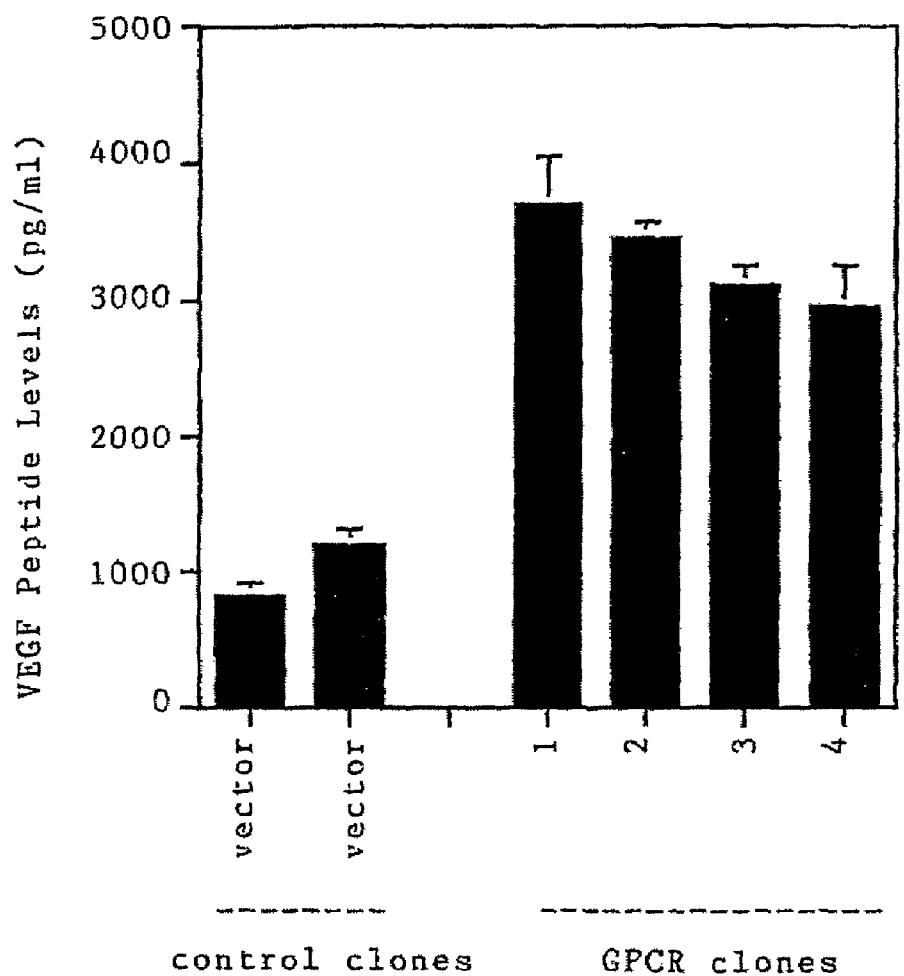
FIG. 6: VEGF peptide levels in conditioned media from GPCR transformed clones. NIH3T3 cells were transformed with pCEFL or GPCR and selected by neomycin (SIGMA). Individual clones were picked, expanded and analysed for VEGF peptide levels as described above.

NIH3T3 cells were transformed with vectors expressing GPCR and the selectable marker "neomycin", individual clones were picked, expanded and analysed for the expression of the VEGF peptide compared to control clones transfected with the empty vector (FIG. 6).

Figure 7:
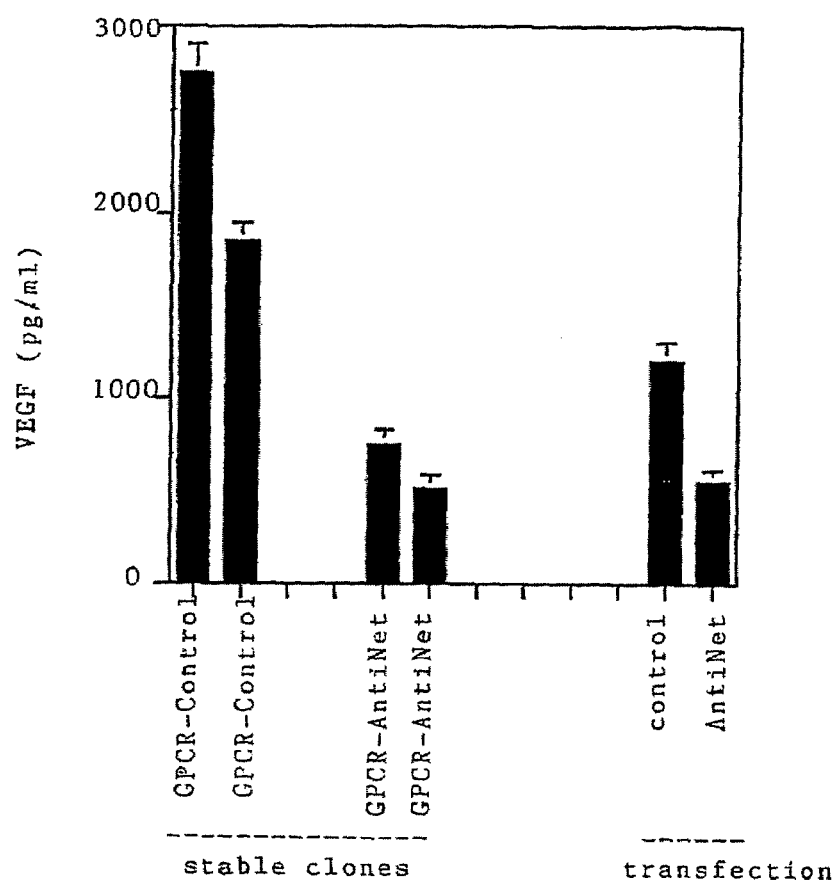
FIG. 7: VEGF peptide levels in conditioned media from pools or isolated GPCR transformed clones transfected with control (p601D) and AntiNet vectors. Several GPCR transformed clones were transformed or transfected with p601D or AntiNet with puromycin expression vectors and treated with 2 nM of puromycin in order to obtain stably transformed GPCR-Control clones; GPCR-AntiNet clones and pool of p601D or AntiNet transfected GPCR clones. VEGF peptide levels were measured by ELISA (Mouse-VEGF Quantikine kit, R&D) and the results were corrected for the cell numbers.

Two typical clones were chosen and re-transformed with a vector expressing antisense net or the control vector together with puromycin resistance, and selected with puromycin (FIG. 7). Several independent clones expressing reduced levels of VEGF peptide were expanded. Analysis of pools of clones transformed with antisense Net showed that its overall effect is to reduce VEGFa secretion, similar to the short term experiments (see FIG. 5).

Figure 8:
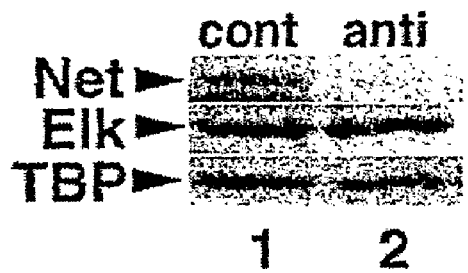
FIG. 8: Net and Elk expression in GPCR-Control and GPCR-AntiNet pools and clones. GPCR clones were transfected with p601D or antiNet with puromycin vectors and selected with puromycin for 48 hours. GPCR-control and GPCR-antiNet clones were grown in Dulbecco's modified Eagle's medium (DMEM) containing 10% fetal calf serum (FCS) for 24 hours (they did not reach confluence). The cells were harvested and extracts were analysed by SDS-PAGE and Western-blotting with antibodies against Net, ELk-1 and TBP. Samples shown are pools (A) or clones (B).
Figure 8:
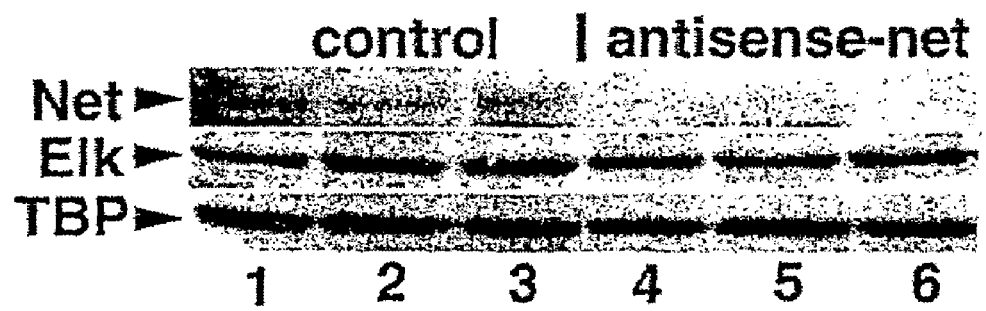

Analysis of the clones by SDS-PAGE and Western blotting showed that Net expression was reduced (see antisense and control clones, FIG. 8; TBP is a control for equal loading).

The expression of Elk1, a protein that is highly homologous to Net (75% at the protein level), was not reduced, showing that the antisense is specific. The antisense also had no effect on the expression of H-Ras and GPCR (data not shown).

These results confirm that when Net activity is stimulated by GPCR, the inhibition of Net expression decreases VEGFa peptide secretion and therefore antisense anti Net can inhibit or reduce angiogenesis through decrease of VEGFa peptide secretion.

Example 6

Down-regulation of Net Inhibits Tumour Formation by GPCR.

In order to study the role of Net in tumour angiogenesis, stable clones of NIH3T3 cells expressing GPCR with or without anti-sense net were prepared (see example 5).

Figure 9:
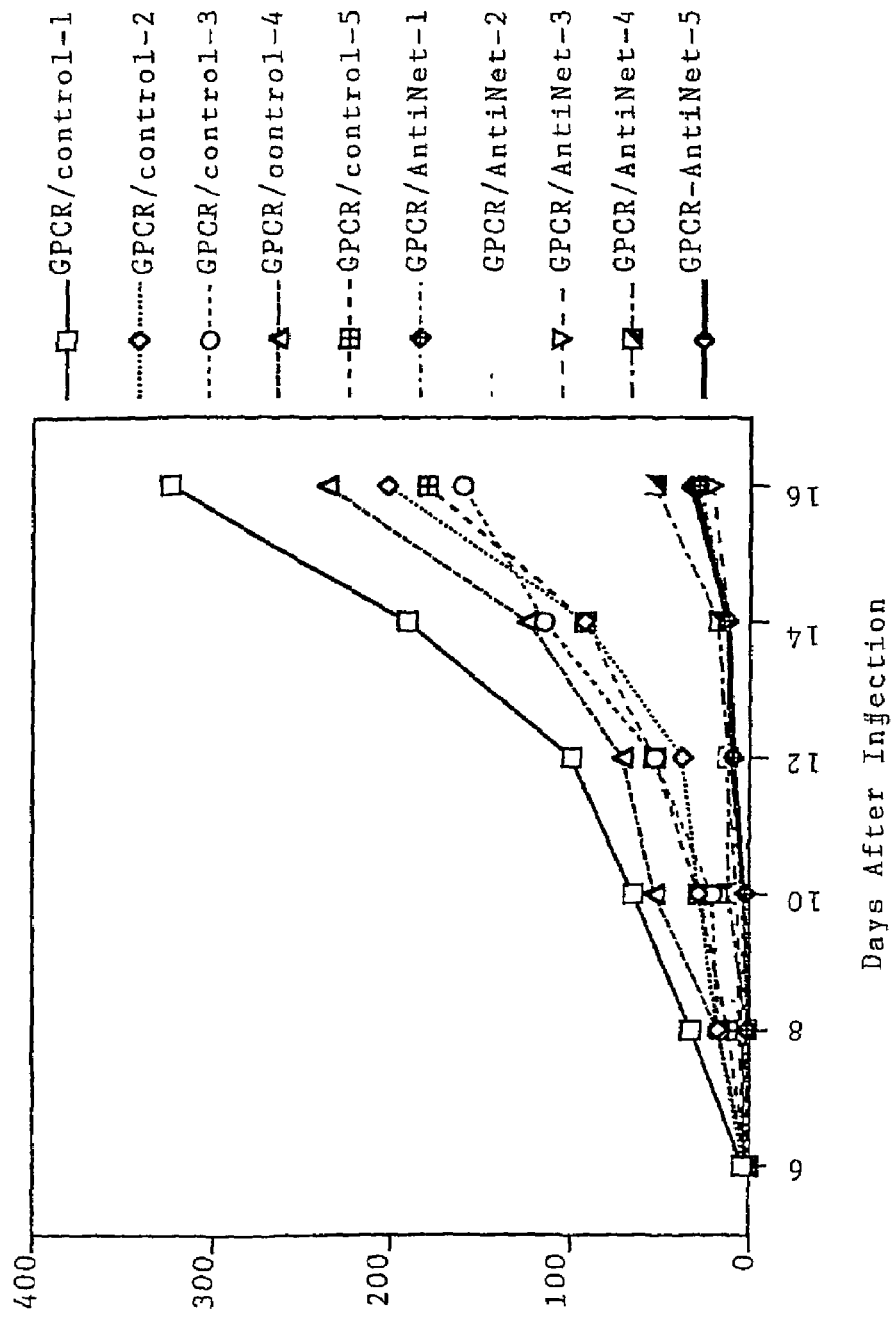
FIG. 9: Volume of tumors formed by GPCR-control and GPCR-AntiNet clones. About $10^6$ cells from different clones were trypsinized, resuspended in PBS and injected subcutaneously in the left flank of 8-10-week-old female BALB/c nu/nu mice (seven mice per clone, two clones for both GPCR-control and GPCR-AntiNet clones). From 6 to 16 days after injection, the smallest and largest tumor diameters were measured every two days with a caliper, and tumour volumes were calculated using the formula: Volume=$(4/3) \times \pi \times (\frac{1}{2} \times \text{smaller diameter} + \frac{1}{2} \times \text{larger diameter})^{2s}$.

Tumour growth was studied in BalbC nu/nu 8 week female mice injected sub-cutaneously with GPCR and GPCR-anti-net clones (about $10^6$ cells per injection). The GPCR clones formed bigger tumours than the GPCR-antisense-net clones (FIG. 9), showing that down-regulation of Net inhibits tumour formation by GPCR.

For the five clones tested, the down regulation of Net induced reduction the volume of tumour by about 70% (from 210 to 30 mm$^3$ on average)

Example 7

Down-regulation of Net Leads to Hypoxic Tumours

Figure 10:
FIG. 10: appearance of tumours generated by GPCR and GPCR anti-Net clones in nude mice. BALB/c nu/nu mice bearing tumours (see legend to FIG. 9) were photographed 16 days after the injection. Arrows point the newly formed blood vessels induced by the tumour. (A) tumour of GPCR clone; (B) tumour of GPCR-antiNet clone.
Figure 10:

It was observed that the GPCR tumours were red in colour and associated with newly formed blood vessels induced by the tumours (FIG. 10; see arrows). In contrast, the GPCR/antisense-net tumours were small with no externally visible blood vessels.

Figure 11:
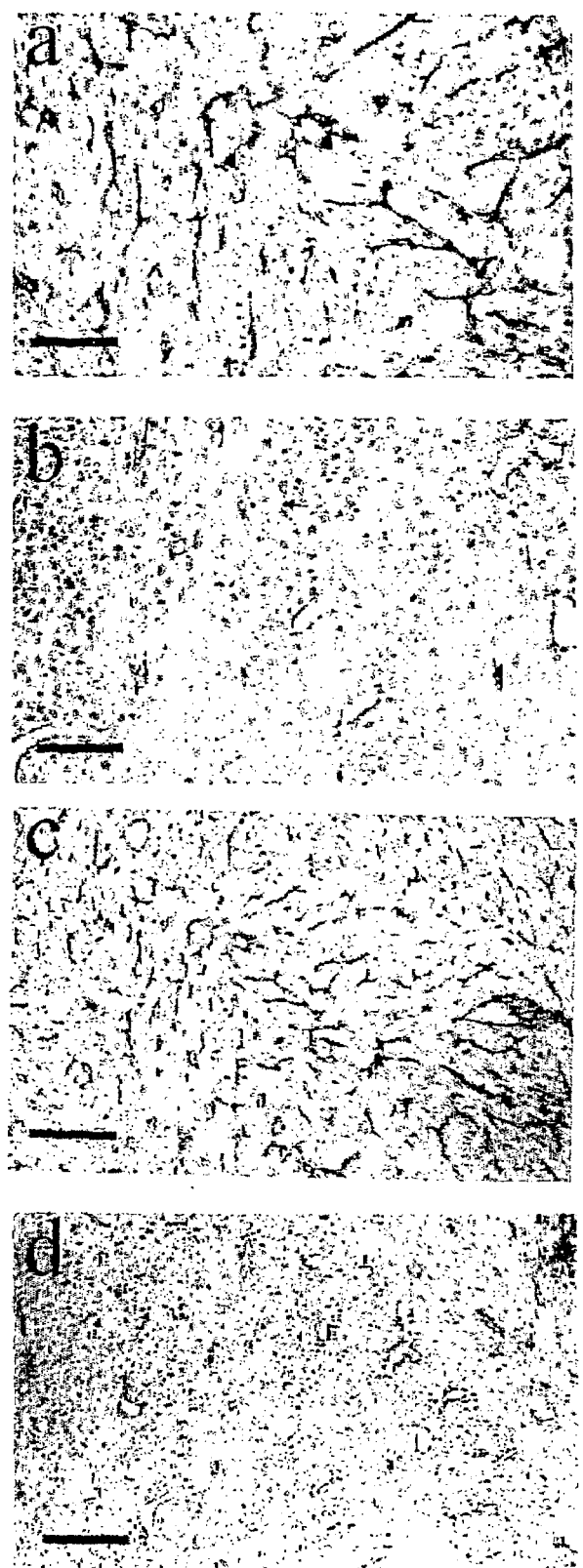
FIG. 11: Vessel density in tumours. Mice were sacrificed 16 days after injection, the tumours were removed and 10 µm paraffin sections were made. Blood vessels in the tumours were detected with antibodies against CD31 (Pharmingen). A dense tumour vasculature was detected in the GPCR tumours (panels a and c), whereas the GPCR/antisense-net tumours had few vessels (panels b and d).
Figure 12:
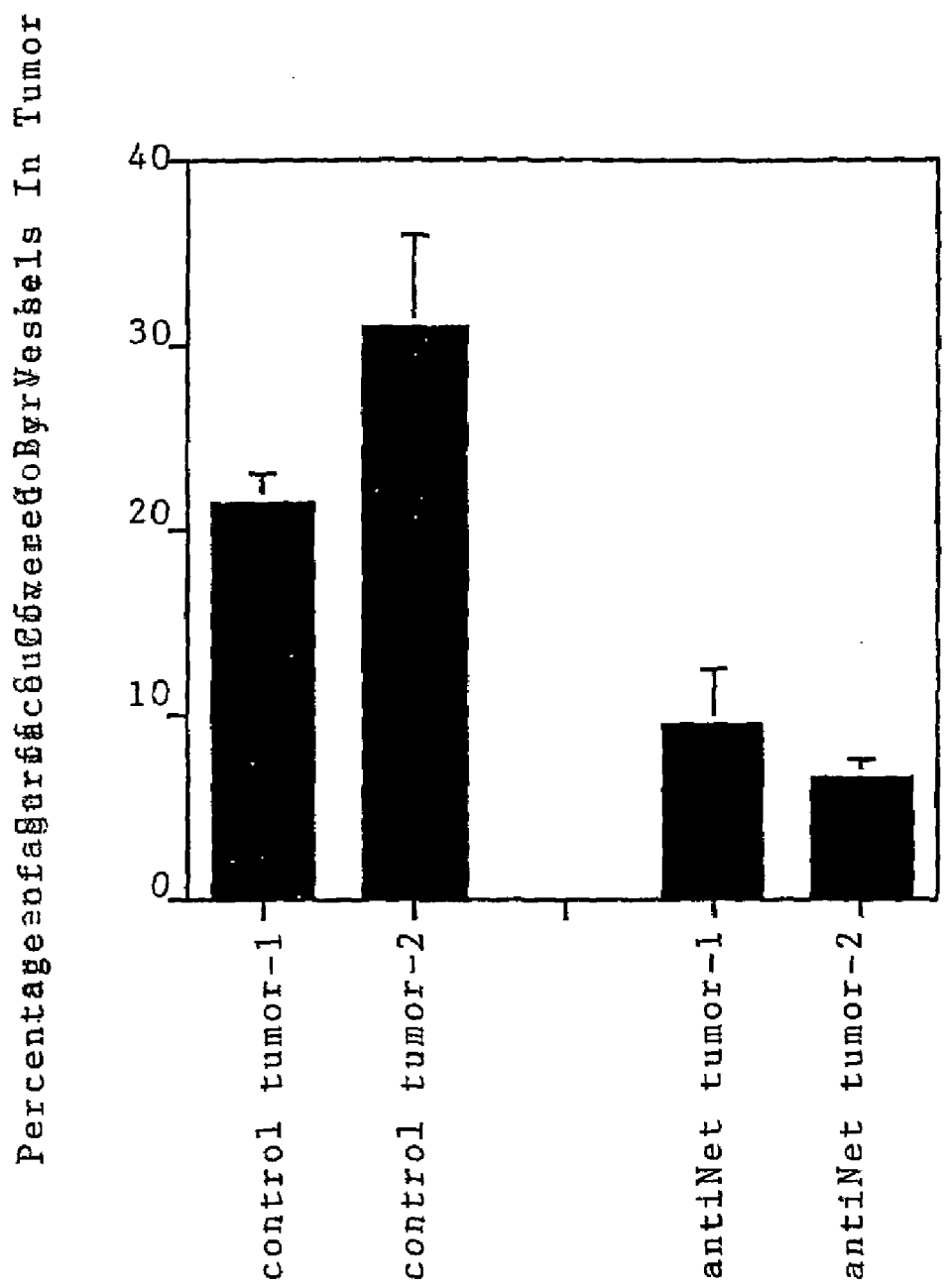
FIG. 12: Vessel covered area in tumors. Parafin sections stained with CD31 obtained from five tumours from each clone were analysed with a computer-controlled microscope. Five randomly selected fields from each section were recorded at ×10 magnification with a digital camera, and morphometric analyses were performed with NSURFX software.
Figure 13:
FIG. 13: Differences of hypoxic tension in tumors. Four hours before the mice were sacrificed, EF5 (Radiation Oncology Imaging Service Center, University of Pennsylvania; 10 mM), a marker of hypoxia, was injected in mice bearing tumours (1 mg/mouse). Cryostat sections (10 µm) were stained with anti-EF5 antibody coupled in Cy5 (Radiation Oncology Imaging Service Center, University of Pennsylvania) and analysed by computer controlled fluorescence microscope with a digital camera. The protocol supplied by the Radiation Oncology Imaging Service Center (University of Pennsylvania) was followed. (A) GPCR-antiNet; (B) GPCR-Vector.
Figure 13:

Blood vessels in the tumours were detected in paraffin sections with antibodies against CD31 (PECAM-1). A dense tumour vasculature was detected in the GPCR tumours (FIGS. 11, a and c), whereas the GPCR/antisense-net tumours had few vessels. The surface area covered by vessels in the GPCR/antisense-net clones was reduced by 75% compared to the GPCR clones (FIG. 12). The reduced vessel density suggests that the tumours formed by the GPCR/antisense-net clones have a lower oxygen level. Tumours were analysed by fluorescence immunohistochemistry against EF5, a surrogate marker for hypoxia (Evans et al., 1997). EF5 (1 mg/mouse) was injected into mice bearing tumours and 4 hrs later sections were prepared, stained with an anti-EF5 antibody coupled to Cy5, and analysed with a computer controlled fluorescence microscope coupled to a digital camera. There were much higher levels of EF5 binding in GPCR/antisense-net clones compared to control GPCR clones (FIG. 13). These data show that GPCR tumours lacking Net are hypoxic, most probably due to the reduced blood vessel density.

Taken together, these results show that Net is required for tumour angiogenesis. These results also demonstrate that inhibitors of NET can provide useful drugs for the treatment of solid tumors.

Example 8

Construction of Mice Bearing Net Gene Deletion (Net δ Mutant Mice).

Figure 14:
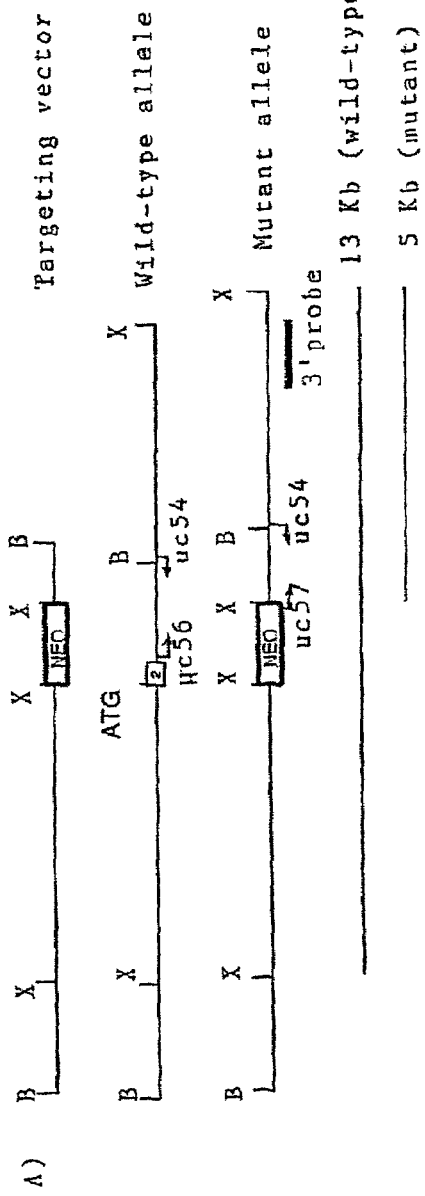
FIG. 14: Targeted mutagenesis of the murine Net locus.
Figure 14:
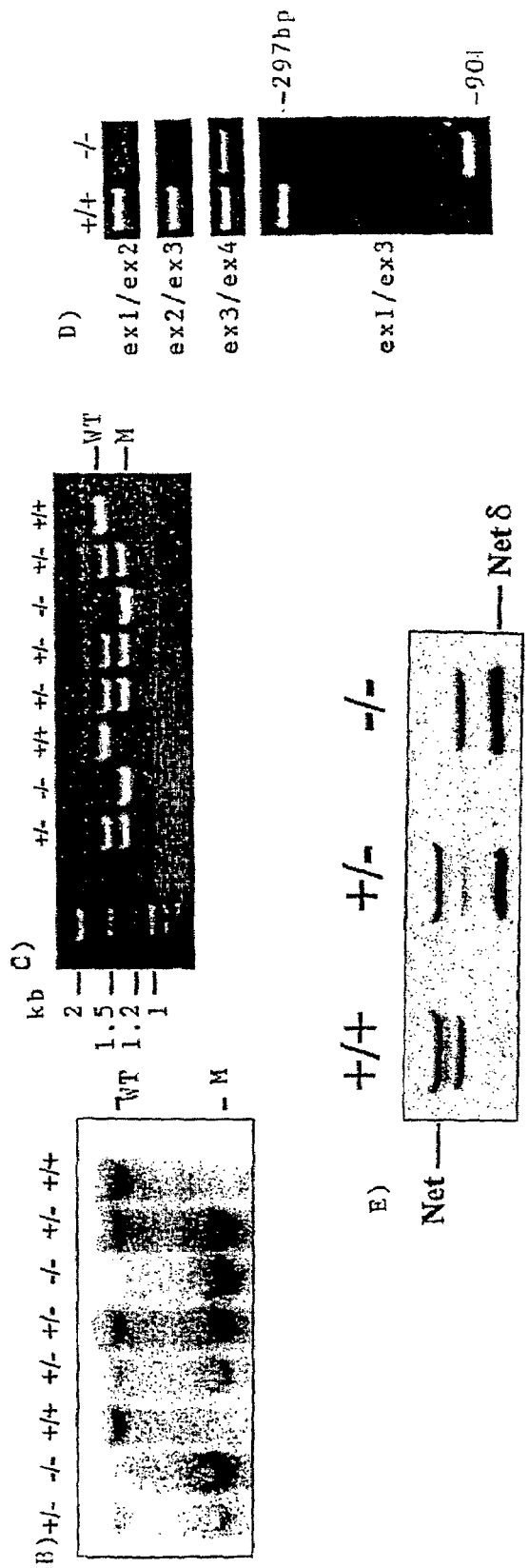

The net gene was modified by homologous recombination in mice. Exon 2, that codes for the DNA binding domain of Net, was replaced by the PGK-neo cassette (FIG. 14A).

Cloning of Net Gene

The net gene was cloned from a λ EMBL3 phage library containing genomic DNA from mouse strain 129/Sv. Clones containing exon 2 were characterised by Southern blot analysis and DNA sequencing.

The targeting vector was constructed by inserting a 11.5-kb BamHI-AvaI fragment from the 5' end of the net genomic clone, a 1.8-kb PGK-neo cassette, and a 1.2-kb AvaI-BamHI fragment from the 3' end of the net genomic clone into pBluescript KS Vector.

Targeted Disruption of the Net Gene

The targeting construct was excised from the vector by NotI digestion and electroporated into D4 ES cells [procedures as described in Deirich and Dollé (1997) Gene targeting in embryonic stem cells. In *Methods in Developmental Toxicology and Biology* (ed. S. T. Klug, R. Thiel) pp 111-123. Blackwell Science]. Genomic DNA from G418 resistant clones was characterised by Southern blot analysis. The DNA was digested with XbaI, and the blots were hybridised with a probe consisting of the 3.8-kb NcoI-NcoI fragment from the 3' end of the net genomic clone. The wild-type allele produces a 13-kb fragment and the mutated allele a 5-kb fragment.

Heterozygous net ES cells were injected into C57BL/6 blastocysts to create chimeric mice. A chimeric mouse that transmitted the mutated Net allele through the germline was used to generate the Net deletion mutant (Net δ) strain mice, on two different genetic backgrounds (129/Sv and C57BL/6). The mice were screened by PCR with genomic DNA from mouse tails with the primers UC54, UC56 and UC57. The wild-type allele generates a 1550-bp fragment and the mutated allele generates a 1300-bp fragment.

```
UC54  TGAAACGTGTAATCCTTGTGTCCTG  (SEQ ID N°5)

UC56  TAATTTCCAAGTTCTCGGCACGTAG  (SEQ ID N°6)

UC57  GACCGCTTCCTCGTGCTTTACGGTA  (SEQ ID N°7)
```

FIG. 14(A) is a schematic representation of the wild type Net allele, the targeting vector and recombinant mutant Net allele. The deleted exon 2 contains the initiation translation codon and encodes amino acids 1-69 in the DNA binding domain of the Net protein. The position of the of the 3' probe used for Southern blot analysis is shown, as well as the XbaI-digested fragments of 13 Kb (wild-type) and 5 kb (mutant allele); B, BamHI; X, XbaI.

The gene was altered, as shown by analysis of mouse DNA by Southern blotting (FIG. 14B) and PCR (FIG. 14C; see FIG. 14A for the primers and probe). FIG. 14(B) displays Southern blot analysis of XbaI-digested DNA from the progeny from a heterozygous (+/−) intercross. Hybridisation using the 3' probe yielded bands corresponding to fragments of 13 kb for the wild-type allele (WT) or 5 kb for the targeted allele M). FIG. 14(C) shows the PCR analysis of the same progeny. The genotype are indicated on the top, the arrows depict the specific amplification products for the wild-type (WT, 1550 bp) and the targeted allele (M, 1300 bp). The PCR primer set (UC54, UC56, UC57) are indicated in the targeting scheme. See material and method: genotyping of ES, embryos and mice.

The mice expressed a novel alternatively spliced mRNA lacking exon 2 (FIG. 14D) and a mutated protein lacking the DNA binding domain resulting from translation initiation in exon 3 (Net δ, FIG. 14E). FIG. 14(D) shows the detection of Net transcripts by RT-PCR. RNA isolated from E16 wild-type and homozygous mutant embryos was used for RT-PCR reactions with primers from different exons of Net gene (exon1 to exon4). The RT-PCR primer sets are indicated on the left part of the panel. As expected with the deletion of exon 2, no amplification is seen in mutant (−/−) RNA with ex1/ex2 or ex2/ex3 sets. However a amplification product is observed between exon 3 and exon 4 (ex3/ex4 set) in the mutant as the wild-type embryo. The RT-PCR reaction between exon1 and exon 3 (ex1/ex3 set) shows that a smaller product (90 bp) exists in the homozygous mutant embryo compared to the wild-type (217 bp). FIG. 14(E) shows Western blot analysis of lung protein extracts from 2 weeks old wild-type, heterozygous and homozygous mice. The amount of the 49-kDA Net protein decreases in the heterozygous (+/−), to fully disappear in the homozygous mutant animal (−/−). However a new 42-kDA protein band appears in the mutant extract (as with the heterozygous).

Example 9

Net Gene Mutation in Mice Affects the Vascular System.

When heterozygous +/δ129Sv mice were crossed, about 25% of the progeny were found to be homozygous for the mutation (FIG. 15A), but within 10 weeks about 90% of the homozygous animals died (FIG. 15B) of respiratory failure due to the accumulation of chyle in the thoracic cage (FIG. 15C), a characteristic of chylothorax. In several instances blood vessel defects were observed, but with low penetrance (data not shown). Histological examination of sections of mice with chylothorax showed that the homozygous mutant mice had dilated lymphatic vessels (lymphangiectasis; FIG. 16, see lv), indicative of defects in lymphatic drainage due to structural or network defects in the circulatory system. The lymphatic vessels were identified using heterozygous VEGF-R3-β-gal knock-in mice that express β-galactosidase in lymphatic vessels (Dumont et al., 1998). On this background, in net δ/δ mice with chylothorax, the lymphatic vessels were dilated in the thoracic cage (FIGS. 17A+B) but not on the heart (C+D) or in the dermis (E+F). Dilated vessels were observed in the thoracic cage of 5 day old δ/δ mice without chylothorax (G & H), and as early as 17.5 dpc (data not shown).

The lymphatic vessel phenotype in 129Sv mice, and the blood vessel phenotype observed in some mice, could be a direct effect of loss of Net function in endothelial cells, where it is highly expressed.

Example 10

Net is Highly Expressed in Endothelial Cells

Net expression was studied during embryogenesis by in-situ hybridisation on whole mounts FIGS. 18, 19) and sections (FIGS. 20, 21). At E7.5, the expression of net and VEGF-R2 (an endothelial cell marker) are quite similar FIGS. 20, B and C). At E8.5 net and VEGF-R2 are co-expressed in the primary capillary plexus of the yolk sac (FIGS. 18, E-F), that is undergoing vasculogenesis, as well as in the endocardium (FIGS. 20, H-I) and in the allantois (FIGS. 18, J & K). At E9.5 and B10.5 they are co-expressed in inter-somitic vessels, in the aorta (FIGS. 19, A B, E, F), and in major head vessels FIG. 19). Later, at E12.5, E14.5, and E16.5, there are many regions of co-expression of net and VEGF-R2, including the tail, liver, heart, lung and intestine (FIGS. 20 G-L), showing that net is highly expressed in endothelial cells. However, there are differences in net and VEGF-R2 expression, notably in that net is highly expressed in regions of cartilage differentiation (FIGS. 21; G-J). Net expression during vasculogenesis and angiogenesis may explain the effect of the net mutation in mice (chylothorax).

Example 11

Egr-1 Gene is a Target Gene for Net

In addition, we have found that Egr-1 is over-expressed in the liver and in some major blood vessels of net δ/δ embryos (data not shown). Egr-1 is an immediate early gene with SRE motifs, and thus this demonstrates that Egr-1 is a target gene for Net.

Interestingly, Egr-1 is implicated in vascular pathology (Silverman and Collins, 1999) and (Yan et al. J. Clin Invest. March 2000;105(5): 553-4). It is required for neointimal formation after mechanical injury resulting notably from angioplasty. It is also necessary for fibrin deposition in vasculature during hypoxemia, apparently through its regulation of tissue factor. There is sustained expression in artherosclerotic lesions, especially in smooth muscle cells. The δ/δ net mice suggest that down-regulation of Net increases Egr-1 activity. Therefore restoring Net repressor activity should be useful in the treatment of restenosis after angioplasty and in the treatment of atherosclerosis.

Example 12

Net Under Normal Conditions is a Repressor of Angiogenesis

The role of Net in angiogenesis was investigated with the corneal pocket technique. This technique has been described by Yoshida et al., (Histol. Histopathol., 14, 1287-1294 (1999)).

Angiogenesis induced by bFGF was reduced in net δ/δ mice compared to their wild type littermates (FIG. 22), showing that Net is required for angiogenesis induced by bFGF.

Angiogenesis was also studied by endothelial cell sprouting from isolated aorta rings under basal conditions. This technique has been described by Brown et al., (Lab. Invest, 75, 539-555 (1996)).

There was increased sprouting from the mutant mice (FIG. 23). This result correlates with the effect of antisense net in serum (basal conditions), which is to relieve Net repression and consequently stimulate VEGF peptide levels (FIG. 5).

These results show that angiogenesis under basal conditions is inhibited by Net. These results also suggest that over-expression of Net, or restoration of Net expression in Net mutated cells will lead to increased control of angiogenesis.

Example 13

Screening for Agents that Modulate Mammalian NET Activity

Results hereabove provide strong evidence for a role for Net in angiogenesis, as an intermediary in the signalling pathways from GPCR or Ras to VEGF production. Compounds that prevent activation of Net by GPCR or Ras should therefore provide useful anti-angiogenic drugs.

Several types of screening assays can be designed such as cellular reporter gene assay, NET/DNA interaction, protein/protein interaction in yeast, phosphorylation assay.

13-A) Cellular Reporter Gene Assay for Gal4-Net(C-Term)/gal4-Reporter Gene (Ras Transformed Cells or Cells Activated by an Angiogenic Stimulus)

This test is described as a generic dual reporter gene assay, cell-based, 384 wells format. Two human transformed cell lines stably transfected with a reporter gene system were obtained:
- a HCT116 clone stably expressing 1) a fusion protein between the GAL4 DNA binding domain and the Net transactivation domain (C-domain) and 2) the Renilla luciferase reporter gene under the control of the GAL4 promoter.
- in order to avoid the selection of molecules that interfere non specifically with the transcriptional activity, a negative control is provided with a SW480 colon carcinoma clone, expressing high levels of the β-catenin protein, and stably expressing the Firefly luciferase reporter gene under the control, in this particular assay, of a T Cell factor/Lef dependent promoter or any other gene reporter assay under control of a promoter unrelated to the Ternary Complex Factor family.

The assay comprises four steps: (i) Plating of the two cell lines of interest onto a 384 well plate, incubation at 37° C. overnight (Medium: D-MEM without phenol red+10% FCS filtered 0.22 μm; (ii), addition of the candidate compounds; (iii), addition of LucLite reagent (Packard, Kit FireLite); Reading of the FireFly luciferase signal on Microbeta™ Trilux (EG&G Wallac) (read out of β-catenin dependent transcription) after 24 hours incubation (negative control) and (iv), addition of RenLite reagent; Reading of the Renilla luciferase signal on Microbeta™ Trilux (EG&G Wallac) (read out of NET dependent transcription).

The molecules of interest inhibit the Renilla luciferase but do not inhibit the firefly activity for the NET assay (Net inhibitors). Activators can also be found in this screening by selecting activator of Renilla activity.

13-B) Net/DNA Interaction:

This property of Net can be evidenced in several experimental setting:
- a gel shift assay (Giovane et al. Gene Dev. 1994, 8, 1502-13).
- the quantitation of a labelled oligonucleotide (2-strands) retained on Net protein. The sequence of the labelled oligonucleotide is derived from the SRE sequence; Net protein can be expressed either partially —DNA interaction domain—or full length in eukaryotic or prokaryotic cells (either in *E. coli* or in baculovirus) and preferentially as a fusion protein (His, HA, GST, myc . . . ) in order to facilitate its purification. The labelled oligonucleotide can be for example SEQ ID No14 5' TCGAGCCGGAAGTGACGTCGA 3' (see Giovane et al. Gene Dev. 1994, 8, 1502-13)

13-C) Protein/Protein Interaction in Yeast:

13-C-1. Interaction Net/SRF on SRE in Yeast

This test consists in the screening of small molecules able to inhibit the transcription dependent on Net, in the yeast *Saccharomyces cerevisiae*, by inhibiting the requirement for Net to previously interact with SRF for binding on SRE.

The yeast strain CL9, that is generally used as screening tool for the 2-hybrid system, is transfected with a reporter system dependent on the GAL4 dependent transcription. The reconstruction through the protein/protein interaction of a functional transcription factor leads to the expression of a reporter gene. Here, this artificial reconstruction of an hybrid transcription factor is only partially required because we use the ability of the proteins of interest to bind a specific SRE sequence on the DNA. in order to avoid having a high background, we use the following constructs:

Net partial cDNA restricted to A and B domains aa 133-265 (DNA binding and SRF binding domain) was cloned into a yeast expression plasmid (with a selection marker)

SRF partial cDNA (restricted to both Net interaction and SRE interaction domains) was cloned in frame with the Gal4 Transactivation domain into the pGAD10 (Clontech) plasmid SRE element 5' TACACAGGATGTCCATATTAGGACA 3' (SEQ ID No15) was cloned as the promoter sequence of a reporter plasmid that leads to the expression of a reporter gene as the beta-galactosidase, URA3 or CAN1, LEU2, HIS3, CYH2, GFP, . . . (the reporter protein has the ability to be detected by a calorimetric, or fluorimetric or enzymatic assay).

These three plasmids (1 µg of each plasmid) were transformed in the yeast strain by a treatment with LiAC/PEG as described by Gietz et al. (1995, studies on the transformation of intact yeast cells by LiAC/SS-DNA/PEG procedure. Yeast, 11: 355-360). The expression of both Net and SRF leads to the expression of the reporter gene, as proteins interact. The yeast strain is permeabilized by the introduction of mutations into either the PDR gene family or into the ERG6 gene. These genes are involved in detoxification processes.

The yeast strain is grown on YNB minimal medium (Yeast Nitrogen Base (without amino-acids)—6,7 g/l; Glucose (20 g/1) with or without agar for support gelification.

Small molecules that inhibit the protein/protein interaction lead to the growth of yeasts lacking the reporter gene activity (calorimetric, sensitivity, . . . ).

This test can be simplified and be restricted to Net-SRF interaction by using in the constructs the respective Net and SRF interaction domains; In this case the corresponding fragments of cDNAs are cloned in the:

PGAD10 (Clontech) plasmid for the expression of a fusion protein with the transactivatory domain of the GAL4 protein (Net-TA or SRF-TA)

The other one is then cloned in the pGBT9 (Clontech) for the expression of a fusion protein with the DNA binding domain of the GALA protein (respectively, SRF-BD or Net-BD).

Here (CL9 strain: The CL9 used for this experiment called reverse 2- hybrid is a cyh2 mutant of the JC981 strain. CYH2 confers the ability to grow in presence of cycloheximide. The CL9 strain was transfected by a plasmid (integrated into the trp1-901 locus) where the wild type CYH2 gene is expressed under the control of the Gal1 (UAS) promoter), the UAS promoter is controlling either the cycloheximide sensitivity and the reporter gene expression.

This test thus consists in a reverse 2-hybrid test in a permeabilized yeast. A small molecule that inhibits the interaction between the proteins leads to the yeast growth on selective growth medium (10 µg/ml cycloheximide).

The molecules are tested by the same protocol on Cycloheximide containing medium.

The test of small molecules consists to grow the transformed yeast on a selective medium containing 10 µg/ml cycloheximide: Droplets of tested molecules are laid onto the surface of the dish and the positive molecules are those that give a growth halo. Positivity is then verified by checking the expression of the reporter gene.

13-C-2) Interaction Net-CtBP:

This second reverse 2-hybrid test is used but, this time, Net cDNA contains also the CID box, on which the interaction domain with the CtBP protein was mapped. SRF cDNA was replaced by CTBP cDNA. The processing of the transformed yeast remains identical.

With regards to examples 13-C-1 and 2, several protocols are available from literature such as described in U.S. Pat. Nos. 5,283,173; 5,468,614; 5,525,490; 5,580,736; 5,885,779.

13-D) Net Phosphorylation:

Net phosphorylation can be quantified either in ELISA or in Cytostar plates (Flashplates) covered by an anti-phospho-Net antibody or in an HTRF assay.

Net is overexpressed, under control of a potent promoter (as for instance the CMV promoter) in a Ras transformed mammalian cell clone stably transfected with an expression vector containing at the same time a selection gene (Hygromycin resistance, Neomycin resistance, . . . ). The Net protein is tagged either at its N-terminus or at its C-terminus with a peptide that can be recognized by a specific monoclonal antibody (Flag, myc-tag, HA, . . . ). The cells are plated into MW96 plates (10000 to 100000 cells per well) and are treated or not by the molecules to be evaluated as inhibitors of Net phosphorylation.

Cells are lysed 24 hours after the addition of the molecules in either BNTG (Hepes 20 mM pH 7.5, NaCl 150 mM, Triton 0,1%, Glycerol 10%, and phosphatase and protease inhibitors: 1 mM Na3VO4, Aprotinin 2,2 µg/ml, 1 µg/ml Leupeptin, 1 µg/ml Antipain, 10 µg/ml Benzamidine, 1 µg/ml Soybean Trypsin Inhibitor, 1 µg/ml Chymostatin, 1 µg/ml Pepstatin-A) or RIPA (50 mM Tris, pH 8.0, NaCl 150 mM, 1% NP-40, 0,5% NaDeoxycholate, 0,1% SDS, 1 mM Na3VO4, 100 µM phenylmethylsulphonyl fluorure (PMSF), 25 µg/ml Aprotinin, 25 µg/ml Leupeptin) buffers.

The cell lysates are then transferred into a MW96 plate previously coated with the monoclonal antibody 2F3. This antibody binds specifically the phosphorylated Net protein.

The experiment is carried on by following the classical ELISA method. The quantitation of the amount of phosphorylated Net in each well is revealed through the binding of a second labelled anti-tag antibody. This labelling allows the quantitation of bound antibody by an enzymatic, or colorimetric, or fluorescent, or radioactive measurement.

An alternative is to label the cell extracts with orthophosphate $P^{33}$ or $P^{32}$ and by incubating the cell lysate in MW96 Cytostar plates (Amersham) previously coated with MoAB 2F3. The bound radioactivity was counted after 3 plate washes in a scintillation counter.

Another alternative to these methods consists in the adaptation of the HTRF screening method by using a labelled europium Kryptate MoAb 2F3. In this case the reagents are added directly in the cell lysate (MoAb 2F3 labelled with europium cryptate and an anti-tag antibody labelled with APC (allophycocyanin)). If simpler, this second antibody can also be biotinylated and we thus add to the reaction mixture APC-streptavidin.

In this assay, the proximity of anti-phosphoNet EuKryptate and anti-tag APC (due to Net phophorylation) produces a fluorescence transfer between Europium and allophycocyanin (APC), when the Europium is excited at 337 nm. Two fluorescence emissions occur: one at 622 nm and the other at 665 nm. The ratio of these fluorescence emissions is then measured: <<(665/622)×10000.

13-E) Use of Net Derived Peptides (D Box) or Net Protein as Substrates in a p38 or ERK Screening Test Based on their Kinase Activity.

For this test a range of peptides or recombinant proteins are produced:

Recombinant mammalian p38 (alpha or beta)
Recombinant mammalian ERK1, ERK2
Recombinant mammalian JNK1, JNK2 or JNK3
These proteins can be fusion proteins (HA-tag or GST so that they can be easily purified after production either in *E. coli* or in baculovirus)

Substrate: A recombinant peptide corresponding to the activation domain of human or murine Net proteins C box or D box (aa 289407 in human) or to the full length Net protein (expressed as previously).

The kinase reaction is carried out in presence of radiolabelled gamma ATP. The reaction mixture is incubated in presence of the molecules during one hour at 30° C. and the reaction is then stopped and the plates are counted in a plate scintilation reader.

A non radioactive adaptation of this protocol is possible by using the previously described fluorescence transfert assay (HTRF).

In this case, the Net substrate should be tagged and the same reagents as described in 13-D could be used after the kinase reaction (done here with cold ATP). If Net is not tagged, it can be biotinylated and the use of streptavidin APC is then required.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

REFERENCES

Arbiser, J. L., Moses, M. A., Fernandez, C A., Ghiso, N., Cao, Y., Klauber, N., Frank D., Brownlee, M., Flynn, E., Parangi, S., Byers, H. R. and Folkman, J. (1997) Oncogenic H-ras stimulates tumor angiogenesis by two distinct pathways. *Proc Natl Acad Sci USA*, 94, 861-866.

Bais, C., Santomasso, B., Coso, O., Arvanitakis, L., Raaka, E. G., Gutkind, J. S., Asch, A. S., Cesarman, E., Gershengorn, M. C., Mesri, E. A. and Gerhengorn, M. C. (1998) G-protein-coupled receptor of Kaposi's sarcoma-associated herpesvirus is a viral oncogene and angiogenesis activator [see comments] [published erratum appears in Nature March 1998 12;392(6672):210]. *Nature*, 391, 86-89.

Boshoff, C. (1998) Kaposi's sarcoma. Coupling herpesvirus to angiogenesis [news; comment]. *Nature*, 391, 24-25.

Brown, K. J., Maynes, S. F., Bezos, A., Maguire, D. J., Ford, M. D. and Parish, C. R. (1996) A novel in vitro assay for human angiogenesis. *Lab Invest*, 75, 539-555.

Dumont, D. J., Jussila, L., Taipale, J., Lymboussaki, A., Mustonen, $T_m$, Pajusola, K., Breitman, M. and Alitalo, K. (1998) Cardiovascular failure in mouse embryos deficient in VEGF receptor-3. *Science*, 282, 946-949.

Evans, S. M., Bergeron, M., Ferriero, D. M., Sharp, F. R., Hermeking, H., Kitsis, R. N., Geenen, D. L., Bialik, S., Lord, E. M. and Koch, C. J. (1997) Imaging hypoxia in diseased tissues. *Adv Exp Med Biol*, 428, 595-603.

Giovane, A., Pintzas, A., Maira, S. M., Sobieszczuk, P. and Wasylyk, B. (1994) Net, a new ets transcription factor that is activated by Ras. *Genes Dev*, 8, 1502-1513.

Silverman, E. S. and Collins, T. (1999) Pathways of Egr-1-mediated gene transcription in vascular biology [comment]. *Am J Pathol*, 154, 665-670.

Yoshida, A., Yoshida, S., Ishibashi, T. and Inomata, H. (1999) Intraocular neovascularization. *Histol Histopathol*, 14, 1287-1294.

What is claimed is:

1. A method for identifying a compound that modulates angiogenesis, said method comprising:
   i) providing a composition comprising a mammalian NET transcription factor;
   ii) contacting the composition with a compound; and
   iii) assessing the ability of said compound to modulate function of said mammalian NET transcription factor;
   wherein the ability of said compound to modulate said mammalian NET transcription factor function identifies said compound as a modulator of angiogenesis.

2. The method according to claim 1, wherein the assessing step comprises detecting modulation of the transcription activity of said mammalian NET transcription factor.

3. The method according to claim 2, wherein detecting modulation of the transcription activity of said mammalian Net transcription factor comprises detecting a change in the level of expression of a reporter gene expressed under control of a chimeric protein consisting of a NET transactivation domain and a DNA binding domain of a transcription factor.

4. The method of claim 3, wherein said DNA binding domain of a transcription factor is a GAL4 DNA binding domain.

5. The method according to claim 3, wherein detecting said change in the level of expression of said reporter gene is in stably transfected mammalian cells.

6. The method of claim 1, wherein the assessing step comprises detecting modulation of a NET/DNA interaction.

7. The method of claim 6, wherein gel shift assay is used to detect modulation of the NET/DNA interaction.

8. The method of claim 6, wherein the DNA that interacts with NET is detectably labeled, and quantifying the amount of the detectably labeled DNA bound to NET is used to detect modulation of the NET/DNA interaction.

9. The method of claim 1, wherein the assessing step comprises detecting a change in NET phosphorylation measured before contact with the candidate compound, and after contact with the candidate compound, wherein said change is a modulation of NET phosphorylation.

10. The method of claim 9, wherein detecting the change in modulation of NET phosphorylation comprises determining NET phosphorylation as a result of kinase activity before and after contact with the candidate compound.

11. The method of claim 10, wherein the kinase is selected from the group consisting of p38α, p38β, ERK1, ERK2, JNK1, JNK2, and JNK3.

12. The method of claim 1, wherein the assessing step comprises determining whether NET or a fragment thereof interacts with a polypeptidic element or nucleic acid after contact with the candidate compound.

13. The method of claim 12, wherein the NET or fragment thereof is the NET SRF binding domain and the polypeptidic element or nucleic acid is SRE.

14. The method of claim 12, wherein the NET or fragment thereof is the NET CtBP binding domain (CID) and the polypeptidic element or nucleic acid is CtBP.

15. The method of claim 1, wherein the composition is a cell or cellular extract.

16. The method according to claim 1, wherein the compound is an agonist of NET.

17. The method according to claim 1, wherein the compound is an antagonist of NET.

* * * * *

UNITED STATES PATENT AND TRADEMARK OFFICE
CERTIFICATE OF CORRECTION

PATENT NO.       : 7,537,887 B2
APPLICATION NO.  : 10/415181
DATED            : May 26, 2009
INVENTOR(S)      : Bohdan Wasylyk et al.

It is certified that error appears in the above-identified patent and that said Letters Patent is hereby corrected as shown below:

On the first page, in field (56), in column 2, under "Other Publications", line 2, delete "specifc" and insert -- specific --, therefor.

On sheet 5 of 25, in Figure 5, line 1, delete "Fron" and insert -- From --, therefor.

In column 1, line 47, delete "targetting" and insert -- targeting --, therefor.

In column 2, line 48, delete "shocks" and insert -- shock --, therefor.

In column 3, line 30, delete "thought" and insert -- through --, therefor.

In column 3, line 55, delete "290-299." and insert -- 290-299, --, therefor.

In column 4, line 29, delete "compound," and insert -- compound; --, therefor.

In column 4, line 45, delete "assessement" and insert -- assessment --, therefor.

In column 4, line 50, delete "assessement" and insert -- assessment --, therefor.

In column 6, line 44, delete "p601D)" and insert -- (p601D) --, therefor.

In column 8, line 2, delete "in" and insert -- to --, therefor.

In column 8, line 57, delete "sacrified" and insert -- sacrificed --, therefor.

In column 9, line 11-17, after "Bars=90 µm)." delete "Bars=90 ?m. The pericardiac (C and D) and chest skin (E and F) lymph vessels in the same animals are not altered in the Net δ/δ mice (Bars=42 µm). In a 5 days-old mice, before the onset of the pleural effusion, the thoracic lymphatic vessels are already dilated in the Net δ/δ (H) compared to the littermate control (G). R, ribs; ic, intercostal region. (Bars=90 µm).".

Signed and Sealed this

Twenty-third Day of November, 2010

David J. Kappos
*Director of the United States Patent and Trademark Office*

CERTIFICATE OF CORRECTION (continued)
U.S. Pat. No. 7,537,887 B2

In column 9, line 19, delete "A)" and insert -- K) --, therefor.

In column 9, line 36, delete "fh," and insert -- fn, --, therefor.

In column 9, line 51, delete "l×," and insert -- lx, --, therefor.

In column 10, line 6, delete "front" and insert -- from --, therefor.

In column 10, line 38, delete "assessement" and insert -- assessment --, therefor.

In column 10, line 66, delete "epithellal" and insert -- epithelial --, therefor.

In column 11, line 17, delete "alzheimer" and insert -- Alzheimer's --, therefor.

In column 11, line 46, delete "fall" and insert -- full --, therefor.

In column 12, line 46, delete "plasmaids," and insert -- plasmids, --, therefor.

In column 12, line 64, delete "550," and insert -- 55°, --, therefor.

In column 15, line 23, delete "I II)." and insert -- I, II). --, therefor.

In column 18, line 12, delete "thyridine" and insert -- thymidine --, therefor.

In column 18, line 24, delete "alkiline" and insert -- alkaline --, therefor.

In column 18, line 29, delete "50:399409" and insert -- 50:399-409 --, therefor.

In column 20, line 6, delete "enterolinase;" and insert -- enterokinase; --, therefor.

In column 24, line 42, after "butadiene" insert -- . --.

In column 24, line 66, delete "Remnington's" and insert -- Remington's --, therefor.

In column 26, line 17, delete "292" and insert -- 292, --, therefor.

In column 26, line 31, delete "polyacrylarnide" and insert -- polyacrylamide --, therefor.

In column 27, line 17, delete "papillornavirus," and insert -- papillomavirus, --, therefor.

In column 33, line 56-57, delete "pCEFLG-PCR" and insert -- pCEFL-GPCR --, therefor.

In column 34, line 9, delete "c," and insert -- 1c, --, therefor.

In column 34, line 35, delete "GPCP" and insert -- GPCR --, therefor.

In column 35, line 32, delete "VEGEa" and insert -- VEGFa --, therefor.

CERTIFICATE OF CORRECTION (continued)
U.S. Pat. No. 7,537,887 B2

In column 38, line 29, delete "M)." and insert -- (M). --, therefor.

In column 41, line 39, delete "in" and insert -- In --, therefor.

In column 41, line 54, delete "calorimetric," and insert -- colorimetric, --, therefor.

In column 42, line 3, delete "calorimetric," and insert -- colorimetric, --, therefor.

In column 42, line 6, delete "domains;" and insert -- domains. --, therefor.

In column 42, line 13, delete "GALA" and insert -- GAL4 --, therefor.

In column 42, line 39, delete "CTBP" and insert -- CtBP --, therefor.

In column 43, line 22, delete "simplier," and insert -- simpler, --, therefor.

In column 43, line 26, delete "phophorylation" and insert -- phosphorylation --, therefor.

In column 43, line 45, delete "289407" and insert -- 289-407 --, therefor.

In column 43, line 51, delete "scintilation" and insert -- scintillation --, therefor.

In column 44, line 2, delete "transfert" and insert -- transfer --, therefor.

In column 43-44, line 1, in Sequence Listing, delete "15" and insert -- 18 --, therefor.

In column 55, line 17, in claim 3, delete "Net" and insert -- NET --, therefor.